US011511106B2

(12) United States Patent
Herb et al.

(10) Patent No.: US 11,511,106 B2
(45) Date of Patent: Nov. 29, 2022

(54) TRANSCUTANEOUS ELECTRICAL NERVE STIMULATION USING NOVEL UNBALANCED BIPHASIC WAVEFORM AND NOVEL ELECTRODE ARRANGEMENT

(71) Applicant: Neurometrix, Inc., Woburn, MA (US)

(72) Inventors: Glenn Herb, Weston, MA (US); Andres Aguirre, Belmont, MA (US); Xuan Kong, Acton, MA (US); Shai N. Gozani, Brookline, MA (US)

(73) Assignee: Neurometrix, Inc., Woburn, MA (US)

( * ) Notice: Subject to any disclaimer, the term of this patent is extended or adjusted under 35 U.S.C. 154(b) by 0 days.

(21) Appl. No.: 17/122,439

(22) Filed: Dec. 15, 2020

(65) Prior Publication Data

US 2021/0205607 A1 Jul. 8, 2021

Related U.S. Application Data

(63) Continuation of application No. 16/175,212, filed on Oct. 30, 2018, now Pat. No. 10,864,365, which is a
(Continued)

(51) Int. Cl.
*A61N 1/04* (2006.01)
*A61N 1/36* (2006.01)
(Continued)

(52) U.S. Cl.
CPC ......... *A61N 1/0452* (2013.01); *A61N 1/0476* (2013.01); *A61N 1/0492* (2013.01); *A61N 1/36034* (2017.08); *A61N 1/0456* (2013.01); *A61N 1/321* (2013.01); *A61N 1/36021* (2013.01); *A61N 1/37247* (2013.01)

(58) Field of Classification Search
CPC .. A61N 1/0456; A61N 1/0452; A61N 1/0476; A61N 1/0492; A61N 1/36034; A61N 1/321; A61N 1/36021; A61N 1/37247
See application file for complete search history.

(56) References Cited

U.S. PATENT DOCUMENTS 1,741,962 A 12/1929 Theodoropulos
4,290,431 A 9/1981 Herbert et al.
(Continued)

FOREIGN PATENT DOCUMENTS

CN 1665563 9/2005
CN 1919139 2/2007
(Continued)

OTHER PUBLICATIONS

Amazon, "Quell 2.0 Wearable Pain Relief Technology", Sep. 15, 2018.http://www.amazon/com/Quell-Wearable-Pain-Relief-Technology/dp/B07DHW2MJJ/ref=cm_cr_arp_d_product_top? ie=UTF8. Shown on p. 1. (Year: 2018).
(Continued)

*Primary Examiner* — Catherine M Voorhees
(74) *Attorney, Agent, or Firm* — Pandiscio & Pandiscio

(57) ABSTRACT

The present invention is directed to transcutaneous electrical nerve stimulation (TENS) devices which utilize novel stimulation waveforms and novel arrangements of TENS electrodes to improve the efficiency of power consumption while enhancing therapeutic effects.

27 Claims, 7 Drawing Sheets

Related U.S. Application Data continuation of application No. 15/350,261, filed on Nov. 14, 2016, now Pat. No. 10,112,040, which is a continuation-in-part of application No. 14/610,757, filed on Jan. 30, 2015, now Pat. No. 9,656,070, which is a continuation of application No. 13/678,221, filed on Nov. 15, 2012, now Pat. No. 8,948,876.

(60) Provisional application No. 61/657,382, filed on Jun. 8, 2012, provisional application No. 61/560,029, filed on Nov. 15, 2011.

(51) Int. Cl.
*A61N 1/32* (2006.01)
*A61N 1/372* (2006.01)

(56) References Cited

U.S. PATENT DOCUMENTS

| | | |
|---|---|---|
| D263,869 S | 4/1982 | Sumiyasu |
| 4,503,863 A | 3/1985 | Katims |
| 4,605,010 A | 8/1986 | McEwen |
| 4,738,250 A | 4/1988 | Fulkerson et al. |
| 4,989,605 A | 2/1991 | Rossen |
| 5,048,523 A | 9/1991 | Yamasawa et al. |
| 5,063,929 A | 11/1991 | Bartelt et al. |
| D323,561 S | 1/1992 | Bartelt et al. |
| 5,121,747 A | 6/1992 | Andrews |
| 5,169,384 A | 12/1992 | Bosniak et al. |
| D342,571 S | 12/1993 | Givens, Sr. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,948,000 A | 9/1999 | Larsen et al. |
| 6,099,488 A | 8/2000 | Hung |
| 6,132,387 A | 10/2000 | Gozani et al. |
| 6,141,587 A * | 10/2000 | Mower .............. A61N 1/36146 607/9 |
| 6,161,044 A | 12/2000 | Silverstone |
| D443,362 S | 6/2001 | Storp |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,611,789 B1 | 8/2003 | Darley |
| 6,662,051 B1 | 12/2003 | Eraker et al. |
| D484,984 S | 1/2004 | Takizawa et al. |
| D534,871 S | 1/2007 | Larsen |
| D541,042 S | 4/2007 | Andre et al. |
| D547,454 S | 7/2007 | Hsieh |
| D566,383 S | 4/2008 | Harris et al. |
| D584,414 S | 1/2009 | Lash et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,016 S | 10/2010 | Potts et al. |
| D625,829 S | 10/2010 | Arbesman et al. |
| D629,115 S | 12/2010 | Robertson |
| 7,887,493 B2 | 2/2011 | Stahmann et al. |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| 8,284,070 B2 | 10/2012 | Chaudhari et al. |
| D677,792 S | 3/2013 | Vandiver |
| D680,735 S | 4/2013 | Itabashi et al. |
| 8,421,642 B1 | 4/2013 | McIntosh et al. |
| D687,951 S | 8/2013 | Della Torre et al. |
| D688,707 S | 8/2013 | Vincent et al. |
| D704,848 S | 5/2014 | Thomas et al. |
| D705,428 S | 5/2014 | Cheney et al. |
| D712,045 S | 8/2014 | Thornton |
| D712,052 S | 8/2014 | Thomas et al. |
| D713,049 S | 9/2014 | Shah |
| 8,825,175 B2 | 9/2014 | King |
| D716,457 S | 10/2014 | Brefka et al. |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| D735,873 S | 8/2015 | Brefka et al. |
| 9,168,375 B2 | 10/2015 | Rahimi et al. |
| D744,661 S | 12/2015 | Rizzi |
| D745,975 S | 12/2015 | Igaue et al. |
| D750,263 S | 2/2016 | Shigeno et al. |
| D750,798 S | 3/2016 | Yosef et al. |
| 9,282,287 B1 | 3/2016 | Marsh |
| 9,282,897 B2 | 3/2016 | Ross, Jr. et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D775,361 S | 12/2016 | Vosch et al. |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| 9,700,724 B2 | 7/2017 | Liu et al. |
| D794,331 S | 8/2017 | Grote |
| 9,731,126 B2 | 8/2017 | Ferree et al. |
| D798,170 S | 9/2017 | Toth et al. |
| D801,542 S | 10/2017 | Anderson |
| D802,780 S | 11/2017 | Hsu |
| 9,827,420 B2 | 11/2017 | Ferree et al. |
| D806,669 S | 1/2018 | Kangasmaa et al. |
| D810,311 S | 2/2018 | Chen |
| D810,843 S | 2/2018 | Karvandi |
| D810,952 S | 2/2018 | Hsu |
| D811,729 S | 3/2018 | Bysshe |
| D813,405 S | 3/2018 | Ho |
| D813,407 S | 3/2018 | Chen |
| D813,408 S | 3/2018 | Chen |
| D821,592 S | 6/2018 | Pham et al. |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |

(56) References Cited

U.S. PATENT DOCUMENTS

| | | | |
|---|---|---|---|
| D832,230 S | 10/2018 | Lee et al. | |
| D834,719 S | 11/2018 | Theriot et al. | |
| D836,788 S | 12/2018 | Peng | |
| D837,394 S | 1/2019 | Cryan et al. | |
| 10,279,179 B2 | 5/2019 | Gozani et al. | |
| 10,335,595 B2 | 7/2019 | Ferree et al. | |
| D857,910 S | 8/2019 | Cryan et al. | |
| D861,903 S | 10/2019 | Cryan et al. | |
| D861,904 S | 10/2019 | Ho | |
| D862,716 S | 10/2019 | Cryan et al. | |
| D865,986 S | 11/2019 | Cryan et al. | |
| D879,983 S | 3/2020 | Wang | |
| 2002/0010497 A1 | 1/2002 | Merfeld et al. | |
| 2003/0023192 A1 | 1/2003 | Foxlin | |
| 2003/0074037 A1 | 4/2003 | Moore et al. | |
| 2003/0114892 A1 | 6/2003 | Nathan et al. | |
| 2003/0208246 A1 | 11/2003 | Kotlik et al. | |
| 2004/0049241 A1 | 3/2004 | Campos | |
| 2004/0122483 A1 | 6/2004 | Nathan et al. | |
| 2005/0059903 A1 | 3/2005 | Izumi | |
| 2005/0080463 A1 | 4/2005 | Stahmann et al. | |
| 2005/0097970 A1 | 5/2005 | Nurse | |
| 2005/0131317 A1 | 6/2005 | Oddsson et al. | |
| 2005/0234525 A1 | 10/2005 | Phillips | |
| 2005/0283204 A1 | 12/2005 | Buhlmann et al. | |
| 2006/0052788 A1 | 3/2006 | Thelen et al. | |
| 2006/0085047 A1 | 4/2006 | Unsworth et al. | |
| 2006/0085049 A1 | 4/2006 | Cory et al. | |
| 2006/0089683 A1 | 4/2006 | Hagglof et al. | |
| 2006/0095088 A1 | 5/2006 | De Ridder | |
| 2006/0173507 A1 | 8/2006 | Mrva et al. | |
| 2006/0190057 A1 | 8/2006 | Reese | |
| 2006/0251334 A1 | 11/2006 | Oba et al. | |
| 2007/0021786 A1 | 1/2007 | Pamis et al. | |
| 2007/0060922 A1 | 3/2007 | Dreyfuss | |
| 2007/0203435 A1 | 8/2007 | Novak | |
| 2007/0203547 A1 | 8/2007 | Costello et al. | |
| 2007/0276449 A1 | 11/2007 | Gunter et al. | |
| 2008/0009772 A1 | 1/2008 | Tyler et al. | |
| 2008/0077192 A1 | 3/2008 | Harry et al. | |
| 2008/0146980 A1 | 6/2008 | Rousso et al. | |
| 2008/0147143 A1 | 6/2008 | Popovic et al. | |
| 2008/0147146 A1 | 6/2008 | Wahlgren et al. | |
| 2008/0172102 A1 | 7/2008 | Shalev | |
| 2008/0312709 A1 | 12/2008 | Volpe et al. | |
| 2009/0030476 A1 | 1/2009 | Hargrove | |
| 2009/0076364 A1 | 3/2009 | Libbus et al. | |
| 2009/0082829 A1 | 3/2009 | Panken et al. | |
| 2009/0112214 A1 | 4/2009 | Philippon et al. | |
| 2009/0131993 A1 | 5/2009 | Rousso et al. | |
| 2009/0203972 A1 | 8/2009 | Heneghan et al. | |
| 2009/0240303 A1 | 9/2009 | Wahlstrand et al. | |
| 2009/0264789 A1 | 10/2009 | Molnar et al. | |
| 2009/0270947 A1 | 10/2009 | Stone et al. | |
| 2009/0326604 A1 | 12/2009 | Tyler et al. | |
| 2010/0004715 A1 | 1/2010 | Fahey | |
| 2010/0010585 A1 | 1/2010 | Davis et al. | |
| 2010/0042180 A1 | 2/2010 | Mueller et al. | |
| 2010/0057149 A1 | 3/2010 | Fahey | |
| 2010/0087903 A1 | 4/2010 | Van Herk et al. | |
| 2010/0094103 A1 | 4/2010 | Kaplan et al. | |
| 2010/0114257 A1 | 5/2010 | Torgerson | |
| 2010/0131028 A1 | 5/2010 | Hsu et al. | |
| 2010/0198124 A1 | 8/2010 | Bhugra | |
| 2010/0217349 A1 | 8/2010 | Fahey | |
| 2010/0241464 A1 | 9/2010 | Amigo et al. | |
| 2010/0274304 A1 | 10/2010 | Wang et al. | |
| 2011/0066209 A1 | 3/2011 | Bodlaender et al. | |
| 2011/0106213 A1 | 5/2011 | Davis et al. | |
| 2011/0166622 A1 | 7/2011 | Crosson et al. | |
| 2011/0190594 A1 | 8/2011 | Heit et al. | |
| 2011/0224665 A1 | 9/2011 | Crosby et al. | |
| 2011/0245711 A1 | 10/2011 | Katra et al. | |
| 2011/0257468 A1 | 10/2011 | Oser et al. | |
| 2011/0264171 A1 | 10/2011 | Torgerson | |
| 2011/0276107 A1 | 11/2011 | Simon et al. | |
| 2011/0282164 A1 | 11/2011 | Yang et al. | |
| 2012/0010680 A1 | 1/2012 | Wei et al. | |
| 2012/0108998 A1 | 5/2012 | Molnar et al. | |
| 2012/0123227 A1 | 5/2012 | Sun et al. | |
| 2012/0130449 A1 | 5/2012 | Carlyon et al. | |
| 2012/0303077 A1 | 11/2012 | De Vincentiis | |
| 2012/0319816 A1 | 12/2012 | Al-Ali | |
| 2013/0096641 A1 | 4/2013 | Strother et al. | |
| 2013/0116514 A1 | 5/2013 | Kroner et al. | |
| 2013/0158627 A1 | 6/2013 | Gozani et al. | |
| 2013/0197341 A1 | 8/2013 | Grob et al. | |
| 2013/0217998 A1 | 8/2013 | Mahfouz et al. | |
| 2013/0317333 A1 | 11/2013 | Yang et al. | |
| 2014/0005759 A1* | 1/2014 | Fahey | A61N 1/0476 607/114 |
| 2014/0039450 A1 | 2/2014 | Green et al. | |
| 2014/0057232 A1 | 2/2014 | Wetmore et al. | |
| 2014/0081353 A1 | 3/2014 | Cook et al. | |
| 2014/0088192 A1 | 3/2014 | Heller et al. | |
| 2014/0107729 A1 | 4/2014 | Sumners et al. | |
| 2014/0163444 A1 | 6/2014 | Ingvarsson et al. | |
| 2014/0206976 A1 | 7/2014 | Thompson et al. | |
| 2014/0221797 A1 | 8/2014 | Bailey et al. | |
| 2014/0245784 A1 | 9/2014 | Proud et al. | |
| 2014/0245791 A1 | 9/2014 | Proud et al. | |
| 2014/0276549 A1 | 9/2014 | Osorio | |
| 2014/0296934 A1 | 10/2014 | Gozani et al. | |
| 2014/0296935 A1 | 10/2014 | Ferree et al. | |
| 2014/0309709 A1 | 10/2014 | Gozani et al. | |
| 2014/0336725 A1* | 11/2014 | Nogueira | A61N 1/0541 607/57 |
| 2014/0336730 A1 | 11/2014 | Simon et al. | |
| 2014/0343625 A1* | 11/2014 | O Laighin | A61N 1/36034 607/48 |
| 2014/0371547 A1 | 12/2014 | Gartenberg et al. | |
| 2014/0371814 A1 | 12/2014 | Spizzirri et al. | |
| 2014/0379045 A1 | 12/2014 | Rahimi et al. | |
| 2015/0045853 A1 | 2/2015 | Alataris et al. | |
| 2015/0100107 A1 | 4/2015 | Kiani et al. | |
| 2015/0157242 A1 | 6/2015 | Sabesan | |
| 2015/0157868 A1 | 6/2015 | Franke et al. | |
| 2015/0174402 A1 | 6/2015 | Thomas et al. | |
| 2015/0238094 A1 | 8/2015 | Lai et al. | |
| 2015/0272511 A1 | 10/2015 | Najafi et al. | |
| 2015/0306387 A1 | 10/2015 | Kong et al. | |
| 2015/0321000 A1 | 11/2015 | Rosenbluth et al. | |
| 2015/0328467 A1 | 11/2015 | Demers et al. | |
| 2015/0335288 A1 | 11/2015 | Toth et al. | |
| 2015/0335877 A1 | 11/2015 | Jeffery et al. | |
| 2016/0007931 A1 | 1/2016 | Rubin et al. | |
| 2016/0113551 A1 | 4/2016 | Annegam et al. | |
| 2016/0144174 A1 | 5/2016 | Ferree et al. | |
| 2016/0151628 A1 | 6/2016 | Simon et al. | |
| 2016/0189371 A1 | 6/2016 | Krishna Rao et al. | |
| 2016/0213924 A1 | 7/2016 | Coleman et al. | |
| 2016/0242646 A1 | 8/2016 | Obma | |
| 2016/0243359 A1 | 8/2016 | Sharma | |
| 2016/0367823 A1 | 12/2016 | Cowan et al. | |
| 2017/0056650 A1 | 3/2017 | Cohen et al. | |
| 2017/0188872 A1 | 7/2017 | Hughes et al. | |
| 2017/0209693 A1 | 7/2017 | An et al. | |
| 2017/0224990 A1 | 8/2017 | Goldwasser et al. | |
| 2017/0368345 A1 | 12/2017 | Kong et al. | |
| 2018/0000685 A1 | 1/2018 | Maloney et al. | |
| 2018/0028808 A1 | 2/2018 | Ferree et al. | |
| 2018/0132757 A1 | 5/2018 | Kong et al. | |
| 2018/0177996 A1 | 6/2018 | Gozani et al. | |
| 2018/0345014 A1 | 12/2018 | Gozani et al. | |
| 2019/0001135 A1 | 1/2019 | Yoo et al. | |
| 2019/0134393 A1 | 5/2019 | Wong et al. | |
| 2020/0179694 A1 | 6/2020 | Kong et al. | |
| 2020/0219615 A1 | 7/2020 | Rabin et al. | |

FOREIGN PATENT DOCUMENTS

| | | |
|---|---|---|
| CN | 1926496 | 3/2007 |
| CN | 101557788 | 10/2009 |
| CN | 101626804 | 1/2010 |

(56) References Cited

FOREIGN PATENT DOCUMENTS

| | | |
|---|---|---|
| CN | 102202131 | 9/2011 |
| CN | 102355847 | 2/2012 |
| CN | 102740919 | 10/2012 |
| DE | 102010052710 | 5/2012 |
| EP | 0971653 | 1/2000 |
| EP | 1 985 277 | 2/2015 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2013/028960 | 2/2013 |
| WO | WO 2014/172381 | 10/2014 |
| WO | WO 2015/123373 | 8/2015 |
| WO | WO 2016/201366 | 12/2016 |
| WO | WO 2018/089655 | 5/2018 |
| WO | WO 2020/033883 | 2/2020 |

OTHER PUBLICATIONS

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Amft, O. et al., Sensing Muscle Activities with Body-Worn Sensors, Conference Paper, May 2006.

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bifulco, P. et al., A Stretchable, Conductive Rubber Sensor to Detect Muscle Contraction for Prosthetic Hand Control, The 6th IEEE International Conference on E-Health and Bioengineering—EHB 2017, Jun. 22-24, 2017, pp. 173-176.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.

Davies HTO et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6): 492-499.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6):639-647.

Fishbain, David A. et al., Transcutaneous Electrical Nerve Stimulation (TENS)Treatment Outcome in Long-Term Users, The Clinical Journal of Pain, Sep. 1996; 12(3):201-214.

Food and Drug Administration, Draft Guidance for Industry and Staff: Class II Special Controls Guidance Document: Transcutaneous Electrical Nerve Stimulator for Pain Relief, Apr. 5, 2010.

Garrison DW et al., Decreased activity of spontaneous and noxiously evoked dorsal horn cells during transcutaneous electrical nerve stimulation (TENS), Pain, 1994, vol. 58: 309-315.

Gilron, I. et al., Chronobiological Characteristics of Neuropathic Pain: Clinical Predictors of Diurnal Pain Rhythmicity, The Clinical Journal Of Pain, 2013.

Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.

Hausdorff, J.M. et al., Gait Variability and Fall Riskin Community-Living Older Adults: A 1-Year Prospective Study, Arch Phys Med Rehabil, Aug. 2001, vol. 82, pp. 1050-1056.

Hori, T. et al., Skin Potential Activities And Their Regional Differences During Normal Sleep In Humans, The Japanese Journal of Physiology, 1970, vol. 20, p. 657-671.

Jelinek HF et al., Electric pulse frequency and magnitude of perceived sensation during electrocutaneous forearm stimulation, Arch Phys Med Rehabil, 2010, vol. 91: 1372-1382.

(56) References Cited

OTHER PUBLICATIONS

Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation forthe management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels And Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement. J. Comp. Physiol. Psychol. Oct. 1959; 52:629-634.
Lykken, D.T., Square-Wave Analysis of Skin Impedance. Psychophysiology. Sep. 1970; 7(2):262-275.
Macfarlane, T. et al., Whether the weather influences pain? Results from EpiFunD study in North West England, Rheumatology, 2010, vol. 49, pp. 1513-1520.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Nightingale, S., The neuropathic pain market, Nature Reviews, 2012, vol. 11, p. 101-102.
Okamoto-Mizuno. K. et al., Effects of thermal environment on sleep and circadian rhythm, Journal of Physiological Anthropology, 2012, vol. 31, No. 14, pp. 1-9.
Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.
Oosterhof, Jan et al., The long-term outcome of transcutaneous electrical nerve stimulation in the treatmentfor patients with chronic pain: a randomized, placebo-controlled trial. Pain Pract. Sep. 2012; 12(7):513-522.
Ossipov MH et al., Central Modulation of Pain, The Journal of Clinical Investigation, Nov. 2010, vol. 120, No. 11, pp. 3779-3787.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy forthe treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Reviewand Cross-Sectional Survey, Diabetes, Metabolic Syndrome and Obesity: Targets and Therapy, 2013, vol. 6, p. 79-92.
Sano, A et al., Quantitative analysis of wrist electrodermal activity during sleep, International Journal of Psychophysiology, 2014, vol. 94, pp. 382-389.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Sheridan et al., Some Factors Influencing the Threshold of the Electrocutaneous Stimulus, Perceptual and Motor Skills, 1966, vol. 22, pp. 647-654.
Susi et al., Motion Mode Recognition and Step Detection Algorithms for Mobile Phone Users, Sensors, Jan. 24, 2013, vol. 13, pp. 1539-1562.
Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977; 15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Waeber, R. et al., Biosection Search with Noisy Responses, SIAM J. Control Optim., 2013, vol. 51, No. 3, pp. 2261-2279.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal Of Pain, 2006, 22(8), p. 681-685.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.
Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.

* cited by examiner

TRANSCUTANEOUS ELECTRICAL NERVE STIMULATION USING NOVEL UNBALANCED BIPHASIC WAVEFORM AND NOVEL ELECTRODE ARRANGEMENT

REFERENCE TO PENDING PRIOR PATENT APPLICATIONS

This patent application is a continuation of prior U.S. patent application Ser. No. 16/175,212, filed Oct. 30, 2018 by Neurometrix, Inc. for TRANSCUTANEOUS ELECTRICAL NERVE STIMULATION USING NOVEL UNBALANCED BIPHASIC WAVEFORM AND NOVEL ELECTRODE ARRANGEMENT, which in turn a continuation of prior U.S. patent application Ser. No. 15/350,261, filed Nov. 14, 2016 by Neurometrix, Inc. for TRANSCUTANEOUS ELECTRICAL NERVE STIMULATION USING NOVEL UNBALANCED BIPHASIC WAVEFORM AND NOVEL ELECTRODE ARRANGEMENT, which in turn is a continuation-in-part of prior U.S. patent application Ser. No. 14/610,757, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application is a continuation of prior U.S. patent application Ser. No. 13/678,221, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which in turn claims benefit of (i) prior U.S. Provisional Patent Application Ser. No. 61/560,029, filed Nov. 15, 2011 by Shai N. Gozani for SENSUS OPERATING MODEL; and (ii) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION.

The six (6) above-identified patent applications are hereby incorporated herein by reference.

FIELD OF THE INVENTION

This invention relates generally to Transcutaneous Electrical Nerve Stimulation (TENS) devices that deliver electrical current across the intact skin of a user via electrodes so as to provide symptomatic relief of chronic pain and other therapeutic benefits. More particularly, this invention discloses the construction of novel TENS stimulation waveforms and novel arrangements of TENS electrodes which improve the efficiency of power consumption while enhancing therapeutic effects.

BACKGROUND OF THE INVENTION

Transcutaneous electrical nerve stimulation (TENS) is the delivery of electricity across the intact surface of the skin to activate underlying nerves; generally with the objective of pain relief. An electrical circuit generates stimulation pulses with specified characteristics. One or more pairs of electrodes, placed on the user's skin, transduce the electrical pulses and thereby stimulate underlying nerves in order to trigger an analgesic response.

Pain relief from TENS stimulation often begins within 15 minutes of the stimulation onset and may last up to an hour following the completion of the stimulation period (also known as a "therapy session"). For optimal pain relief, each therapy session should run for at least 30 minutes and preferably 60 minutes. To maintain pain relief (i.e., analgesia), TENS therapy sessions typically need to be initiated at regular intervals, such as every other hour. Newly developed wearable TENS devices such as the QUELL® device by Neurometrix, Inc. of Waltham, Mass., USA provide users with an option to automatically restart therapy sessions at pre-determined time intervals.

Battery life is an engineering challenge in portable devices. The waveform of the stimulation pulse has a significant impact on the battery life of a TENS device. Symmetric biphasic rectangular pulses are often used in TENS devices but such pulse waveforms may not be optimal for maximizing battery life.

The present invention is directed to TENS devices which utilize novel stimulation waveforms and novel arrangements of TENS electrodes to improve the efficiency of power consumption while enhancing therapeutic effects.

SUMMARY OF THE INVENTION

The present invention is directed to transcutaneous electrical nerve stimulation (TENS) devices which utilize novel stimulation waveforms and novel arrangements of electrodes to improve the efficiency of power consumption while enhancing therapeutic effects.

In one preferred form of the present invention, there is provided apparatus for providing transcutaneous electrical nerve stimulation to a user, said apparatus comprising:

a housing;

a stimulation unit for electrically stimulating nerves using asymmetric biphasic electrical pulses, wherein during each phase of an asymmetric biphasic electrical pulse, said stimulation unit generates a voltage at an anode that is higher than a voltage at a cathode so as to allow current to flow from the anode to the cathode, and wherein said stimulation unit delivers a larger amount of electrical charge in the second phase of the asymmetric biphasic electrical pulse than the amount of electrical charge delivered in the first phase of the asymmetric biphasic electrical pulse using the same anode voltage setting in both phases of the asymmetric biphasic electrical pulse by taking advantage of the electrical charge accumulated during the first phase of the asymmetric biphasic electrical pulse;

a control unit for controlling the electrical stimulation delivered by said stimulation unit; and an electrode array connectable to said stimulation unit, said electrode array comprising a substrate and at least first and second electrodes, the at least first and second electrodes being mounted to said substrate with a predetermined arrangement, such that when said substrate is placed on the user, said first electrode overlays a first nerve but not a second nerve and said second electrode overlays the second nerve but not the first nerve.

In another preferred form of the present invention, there is provided apparatus for providing transcutaneous electrical nerve stimulation to a user, said apparatus comprising:

a housing;

a stimulation unit for electrically stimulating nerves using asymmetric biphasic electrical pulses, wherein said stimulation unit delivers a larger amount of electrical charge in the second phase of the asymmetric biphasic electrical pulse than the amount of electrical charge delivered in the first phase of the asymmetric biphasic electrical pulse using the same voltage output level by taking advantage of the electrical charge accumulated during the first phase of the asymmetric biphasic electrical pulse;

a control unit for controlling the stimulation delivered by said stimulation unit; and an electrode array connectable to said stimulation unit, said electrode array comprising a substrate and at least first and second electrodes, the at least first and second electrodes being mounted to said substrate with a predetermined arrangement, such that when said substrate is placed on the user, said first electrode overlays a first nerve but not a second nerve and said second electrode overlays the second nerve but not the first nerve.

In another preferred form of the present invention, there is provided a method for providing transcutaneous electrical nerve stimulation therapy to a user, said method comprising:

providing a stimulation unit for generating asymmetric biphasic electrical pulses, wherein the asymmetric biphasic electrical pulses are generated by creating a voltage difference between an anode voltage and a cathode voltage, and the amount of electrical charge delivered in the second phase of an asymmetric biphasic electrical pulse is larger than the amount of electrical charge delivered in the first phase of the asymmetric biphasic electrical pulse using the same anode voltage during the first and second phases of the asymmetric biphasic electrical pulse by taking advantage of the electrical charge accumulated during the first phase of the asymmetric biphasic electrical pulse;

providing an electrode array connectable to said stimulation unit, said electrode array comprising a substrate and at least first and second electrodes, the at least first and second electrodes being mounted to said substrate with a predetermined arrangement, such that when said substrate is placed on the user, said first electrode overlays a first nerve but not a second nerve and said second electrode overlays the second nerve but not the first nerve; and using said stimulation unit and said electrode array to apply asymmetric biphasic electrical pulses to the skin of a user.

In another preferred form of the present invention, there is provided a method for providing transcutaneous electrical nerve stimulation to a user, the method comprising:

providing a stimulation unit for generating asymmetric biphasic electrical pulses, wherein said stimulation unit delivers a larger amount of electrical charge in the second phase of the asymmetric biphasic electrical pulse than the amount of electrical charge delivered in the first phase of the asymmetric biphasic electrical pulse without increasing the voltage output of said stimulator unit by taking advantage of the electrical charge accumulated during the first phase of the asymmetric biphasic electrical pulse, and providing an electrode array connectable to said stimulation unit, said electrode array comprising at least first and second electrodes;

placing the electrode array on the user so that the first electrode overlays a first nerve but not a second nerve and the second electrode overlays the second nerve but not the first nerve; and using said stimulation unit to apply asymmetric biphasic electrical pulses to the skin of the user.

In another preferred form of the present invention, there is provided apparatus for providing transcutaneous electrical muscle stimulation to a user, said apparatus comprising:

a housing;

a stimulation unit for electrically stimulating muscles using an asymmetric biphasic electrical pulse, wherein during each phase of an asymmetric biphasic electrical pulse, said stimulation unit generates a voltage at an anode that is higher than a voltage at a cathode so as to allow current to flow from the anode to the cathode, and said stimulation unit delivers a larger amount of electrical charge in the second phase of the asymmetric biphasic electrical pulse than the amount of electrical charge delivered in the first phase of the asymmetric biphasic electrical pulse using the same anode voltage setting in both phases of the asymmetric biphasic electrical pulse by taking advantage of the electrical charge accumulated during the first phase of the asymmetric biphasic electrical pulse;

a control unit for controlling the stimulation delivered by said stimulation unit; and an electrode array connectable to said stimulation unit, said electrode array comprising a substrate and at least first and second electrodes, the at least first and second electrodes being mounted to said substrate with a predetermined arrangement, such that when said substrate is placed on the user, said first electrode overlays a first muscle but not a second muscle and said second electrode overlays the second muscle but not the first muscle.

In another preferred form of the present invention, there is provided a method for providing transcutaneous electrical muscle stimulation therapy to a user, said method comprising of the steps of:

placing an electrode array on the skin of a user so that a first electrode of said electrode array overlays a first muscle but not a second muscle and so that a second electrode of said electrode array overlays the second muscle but not the first muscle;

controlling a stimulator unit to generate asymmetric biphasic electrical pulses; and delivering said asymmetric biphasic electrical pulses to the electrode array, wherein the second phase of the asymmetric biphasic electrical pulses delivers a larger amount of electrical charge than the first phase of the asymmetric biphasic electrical pulses without the need to increase the output voltage of the stimulator unit during the second phase of the asymmetric biphasic electrical pulses by taking advantage of the electrical charge accumulated during the first phase of the asymmetric biphasic electrical pulse.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

TENS in General

Figure 1:
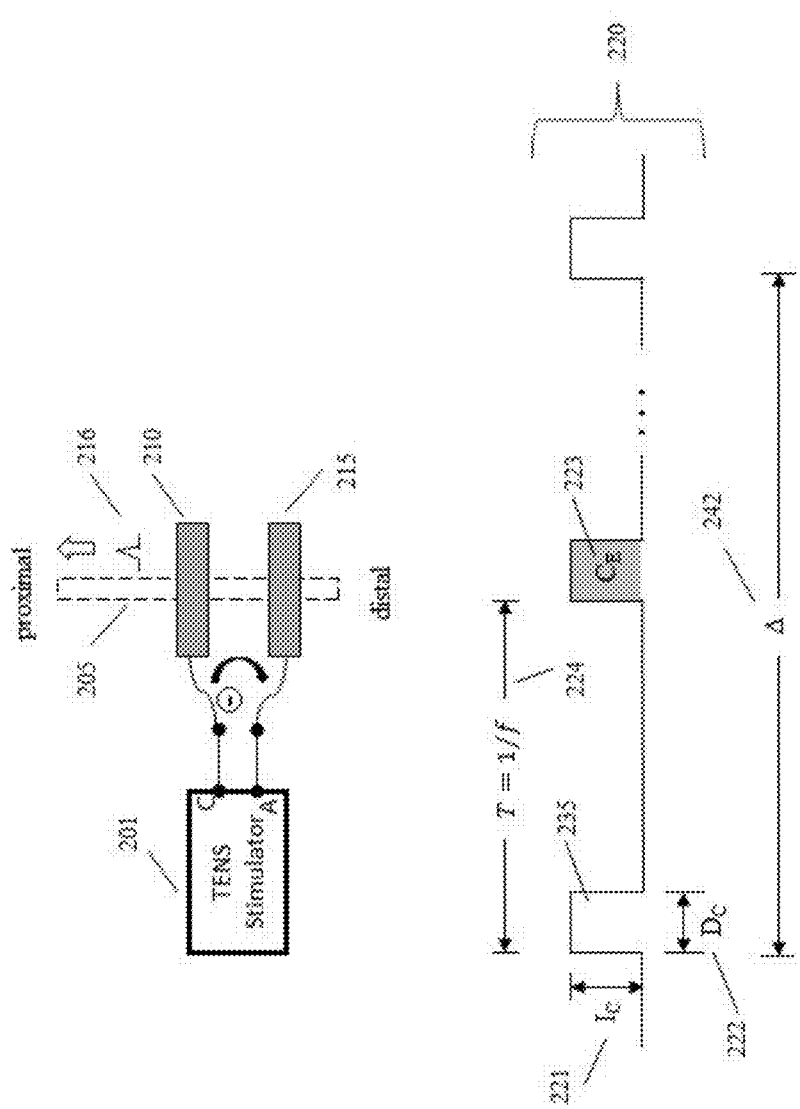
FIG. 1 is a schematic view of a traditional TENS stimulator using monophasic stimulation pulses to stimulate a nerve via a conventional electrode arrangement.

Transcutaneous electrical nerve stimulation, typically abbreviated as TENS, is the delivery of electricity across the intact surface of the skin so as to activate underlying nerves, generally with the objective of pain relief. A conceptual model for how peripheral nerve stimulation leads to pain relief was proposed by Melzack and Wall in 1965 (Melzack R, Wall P D. Pain mechanisms: a new theory. Science. Nov. 19, 1965; 150(699):971-979). Their theory suggests that the activation of sensory nerves (Aβ fibers) closes a "pain gate" in the spinal cord which inhibits the transmission of pain signals carried by nociceptive afferents (C and Aδ fibers) to the brain. In the past 20 years, the anatomic pathways and molecular mechanisms that may underlie the pain gate have been elucidated. Sensory nerve stimulation activates the descending pain inhibition system, primarily the periaqueductal gray (PAG) and rostroventral medial medulla (RVM) located in the midbrain and medulla sections of the brainstem, respectively (DeSantana J M, Walsh D M, Vance C, Rakel B A, Sluka K A. Effectiveness of transcutaneous electrical nerve stimulation for treatment of hyperalgesia and pain. Curr Rheumatol Rep. December 2008; 10(6):492-499). The PAG has neural projections to the RVM, which in turn has diffuse bilateral projections into the spinal cord dorsal horn (Ossipov M H, Dussor G O, Porreca F. Central modulation of pain. J Clin Invest. November 2010; 120(11): 3779-3787). Peripheral nerve stimulation activates the PAG, which triggers the RVM to broadly inhibit pain signal transmission in the spinal cord dorsal horn. Although it is activated by localized peripheral nerve stimulation, the descending pain inhibition system has analgesic effects that may extend beyond the stimulation site to provide broad pain relief (Dailey D L, Rakel B A, Vance C G, et al. Transcutaneous electrical nerve stimulation reduces pain, fatigue and hyperalgesia while restoring central inhibition in primary fibromyalgia. Pain. November 2013; 154(11):2554-2562).

As described above, TENS induces analgesia by stimulating peripheral nerves. A peripheral nerve is defined as a nerve, which is a collection of nerve fibers (i.e., axons), that is outside of the brain and spinal cord. Peripheral nerves may comprise nerve fibers that provide sensory, motor or autonomic functions. TENS is primarily intended to stimulate somatic peripheral nerves, meaning nerve fibers that either bring sensory information into the nervous system or carry motor control information to the muscles. As peripheral nerves descend from the spinal cord they may break off into various branches. Some of these branches may be large enough that they are named peripheral nerves. For example, the sciatic nerve, which is formed from spinal nerves in the lumbosacral region, travels all the way from the lower back to the knee as one major nerve. In the popliteal fossa (i.e., behind the knee) it branches into the tibial nerve and the common peroneal nerve. These two nerves then branch into additional nerves further down the leg and into the foot. Most peripheral nerve branches are smaller and provide limited function such as innervating a muscle or providing sensation to a particular area of skin. In the latter case, the branch may be described as a cutaneous branch. In some cases, small branches of peripheral nerves are called collaterals.

TENS is characterized by a number of stimulation parameters including the stimulation pulse shape, amplitude, duration, pattern, and frequency. Increasing pulse amplitude or duration, or both, increases the pulse intensity (intensity=amplitude*duration) of the TENS therapy. For the same intensity, the relative effectiveness of the stimulation pulse decreases with longer duration due to the strength-duration relation of a nerve. Stimulation at an intensity below the level of sensory perception does not provide pain relief, and the degree of analgesia is correlated to the stimulation intensity. Scientific studies and clinical experience suggest that therapeutically effective TENS occurs at an intensity that feels "strong but comfortable" to the user.

Looking now at FIG. 1, the dose of the TENS therapy is approximately defined as $C_E*f*\Delta$. Quantity $C_E$ 223 is the effective charge per pulse, or the portion of total pulse charge that is actually effective in stimulating nerve fibers with the resulting nerve pulses traveling proximally to the central nervous system. Quantity f is the pulse frequency, and its inverse is the pulse period T 224. Quantity $\Delta$ 242 is the therapy session duration. Pulse frequency f is limited by the frequency response of the nerve, which is determined by the temporal excitability profile of the nerve including its refractory period, and the frequency response of the central neural circuits associated with analgesia. In general, analgesic efficacy drops off over about 100 Hz. Therapy session duration $\Delta$ 242 is limited by patient preferences and by the physiology of the endogenous opioid system, where opioid concentration starts to drop after about 1 hour of stimulation.

To stimulate a peripheral nerve 205, a TENS stimulator 201 needs at least two separate contact areas with the skin (e.g., cathode electrode 210 and anode electrode 215) so that a closed circuit can be formed. Hydrogel-based electrodes (e.g., cathode electrode 210 and anode electrode 215) are preferably used to create the electrical interface between the TENS stimulator and the skin in the contact areas. Important parameters for electrical pulses are amplitude $I_C$ 221 and duration $D_C$ 222. For each monophasic pulse 235, its intensity or total pulse charge $IN_C$ is defined as the product of $I_C$ and $D_C$: $IN_C=I_C*D_C$. The nerve segment under cathode electrode 210 is activated by an electrical pulse when the intensity $IN_C$ exceeds a threshold. The exact threshold value depends upon many factors, including the user's age, height and weight, biophysical characteristics of the nerve being stimulated, and electrode geometry. In general, the stimulation current amplitude $I_C$ 221 must also be above a minimum value called the rheobase to activate the nerve segment under the electrode. For a sequence of monophasic pulses 220, each pulse with the total pulse charge $IN_C$ contributes effectively to the activation of the nerve impulse 216 that travels proximally along the nerve. Therefore, the effective charge $C_E$ 223 equals the total pulse charge: $C_E=IN_C=I_C*D_C$ in the case of monophasic pulse TENS.

Although monopolar stimulation pulses 220 are efficient in that the effective charge is equal to the pulse charge, monopolar stimulation pulses are not generally used in TENS stimulation due to known adverse skin reactions under anode 215 and cathode 210 following a prolonged period of stimulation. More particularly, during stimulation, negatively charged ions in the skin will be attracted towards the anode electrode and their excessive accumulation will cause an acid reaction in the skin area under the anode 215. Similarly, positively charged ions in the skin will move to the cathode electrode and their excessive concentration will cause an alkaline reaction in the skin area under the cathode 210. To overcome these adverse skin reactions, biphasic stimulation pulses are typically used in modern TENS devices.

Figure 2:
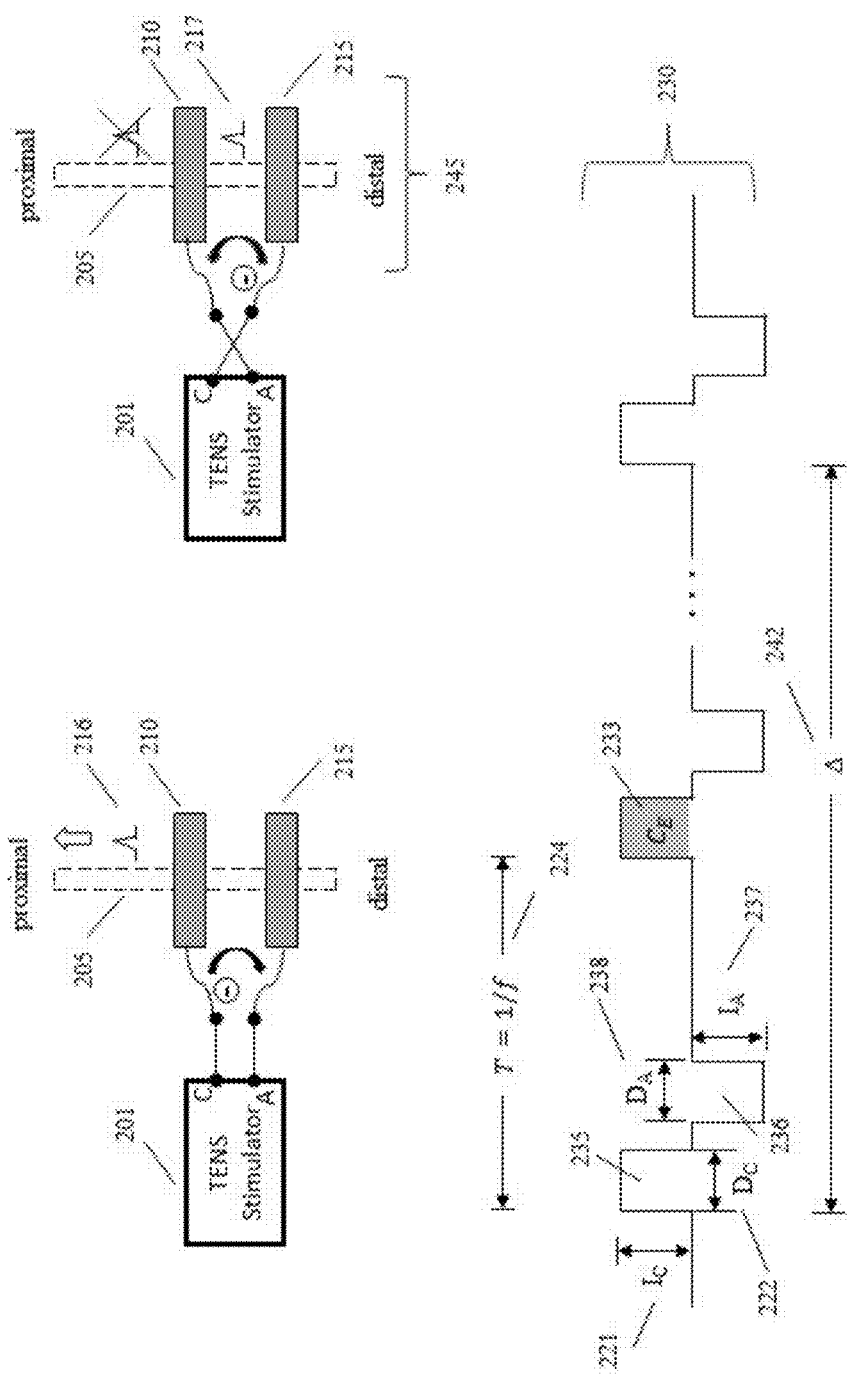
FIG. 2 is a schematic view of a traditional TENS stimulator using biphasic stimulation pulses to stimulate a nerve via the conventional electrode arrangement shown in FIG. 1.

Looking now at FIG. 2, the biphasic pulses 230 typically used in modern TENS devices (e.g., TENS stimulator 201) have a second phase 236 following the first phase 235 for each stimulation pulse. The second phase 236 of the biphasic pulse serves a primary purpose of balancing the charge delivered during the first phase 235 of the biphasic pulse, thereby preventing adverse skin reactions due to the build-up of charged ions under the electrodes. Electrically, the second phase 236 of the biphasic pulse reverses the roles of the anode and cathode, but no effective nerve stimulation should be expected under the "new" cathode (i.e., electrode 215) with the electrode arrangement shown in 245. There are two reasons for this. First, the nerve segment under electrode 215 is hyperpolarized during the first phase 235 of the biphasic pulse, making it more difficult to be activated by the stimulation current $I_A$ 237 in the second phase 236 of the biphasic pulse. Second, even if the nerve segment under electrode 215 could be activated by the second phase 236 of the biphasic stimulation pulse, any resulting nerve pulses 217 could not travel proximally (i.e., towards the central nervous system) past electrode 210 because of the refractory period of the nerve segment located under electrode 210. More particularly, the refractory period refers to the inability of a nerve fiber to transmit a second pulse within a certain time period of the first pulse passing through the nerve segment. The refractory period for a human peripheral nerve is generally on the order of several milliseconds, while the delay between the two phases of a TENS biphasic pulse is usually less than one-tenth of a millisecond. Hence, the second phase 236 of the biphasic pulse is delivered to electrode 215 and activates a nerve pulse 217 originating from the nerve segment under electrode 215. Because the nerve segment under electrode 210 is still in its refractory period due to nerve pulse activation earlier from the first phase 235 of the biphasic pulse, the nerve pulse 217 is prevented from traveling through the nerve segment under the electrode 210 in the proximal direction. As a result, the second phase 236 of the biphasic pulse does not provide the beneficial effect of activating any nerve pulse that can travel proximally to contribute to pain relief. In this case, the effective charge is still $C_E = I_C * D_C$, even though the biphasic pulses have a total pulse charge of $(I_C * D_C + I_A * D_A)$, i.e., the pulse charge $I_C * D_C$ of the first phase of the biphasic pulse plus the pulse charge $I_A * D_A$ of the second phase of the biphasic pulse. In other words, the effective charge $C_E$ 233 of the biphasic pulse is essentially just the pulse charge of the first phase of the biphasic pulse, and the second phase of the biphasic pulse does not produce effective nerve stimulation. However, as noted above, the use of biphasic pulses is nonetheless beneficial to overcome adverse skin reactions under the electrodes, and hence has often been adopted with TENS devices.

Figure 3:
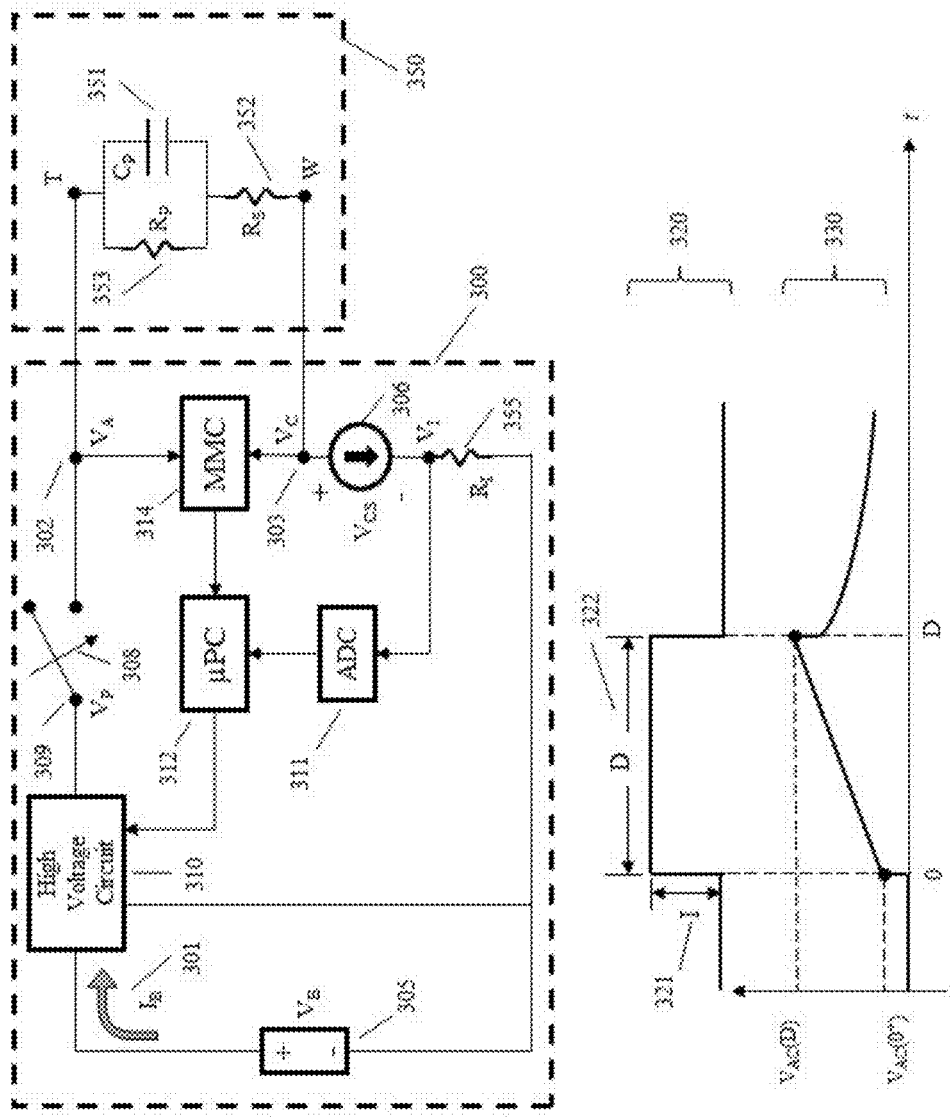
FIG. 3 is a schematic view of a novel TENS stimulator formed in accordance with the present invention.

FIG. 3 provides a functional block diagram for a novel TENS stimulator 300 when connected to a patient load 350. Novel TENS stimulator 300 is configured to provide biphasic pulses in accordance with the present invention, however, for clarity of illustration, FIG. 3 shows only the first phase of a biphasic pulse generated by novel TENS stimulator 300 (and omits the second phase of the biphasic pulse). Switch 308 can be open when the TENS stimulator is not delivering current to the patient load. The load to the TENS stimulator output terminals (i.e., anode terminal 302 and cathode terminal 303) consists of the electrodes, body tissue, and the interface between the electrodes and skin (note that, even though TENS stimulator 300 is configured to deliver biphasic pulses, terminal 302 is referred to as the "anode" terminal, and terminal 303 is referred to as the "cathode" terminal, since they typically serve this function during the first phase of the biphasic pulse). A common and effective circuit model of the skin-electrode contact and tissue volumetric impedance (i.e., the load to the stimulator) is a resistor in series with a parallel resistor-capacitor (RC) circuit as shown inside 350. When switch 308 is closed, anode terminal voltage $V_A$ at the anode terminal 302 is the same as the high voltage circuit voltage $V_P$ at the high voltage circuit output 309. In order to deliver an electrical stimulation pulse 320 with a target current amplitude I 321 for a duration D 322, a minimum voltage bias $V_{CS}^{min}$ must be maintained at the current source 306. The voltage $V_{AC} = V_A - V_C$ between anode terminal 302 (i.e., the anode electrode connector) and cathode terminal 303 (i.e., the cathode electrode connector), as a result of a stimulation current pulse with amplitude I 321, is given by $$\tau * \frac{dV_{AC}}{dt} = -V_{AC} + I * (R_S + R_P)$$

where the time constant $\tau = R_P * C_P$, i.e., a product of capacitor value $C_P$ of a capacitive component 351 and resistor value $R_P$ of a resistive component 353. Resistor value $R_S$ is for a resistive component 352 of the patient load. The above equation has the solution $$V_{AC}(t) = I * [R_S + R_P * (1 - e^{-t/\tau})], \ 0 \le t \le D$$

Using $R_S = 200\Omega$, $R_P = 130$ k$\Omega$, $C_P = 0.1$ µF (an equivalent circuit model of a healthy subject electrode-skin interface) gives $\tau = 13$ milliseconds. Stimulation current pulse duration D 322 has a typical range of 100-200 microseconds, so we have $D \ll \tau$. Given that $t < D \ll \tau$, $V_{AC}(t)$ can be approximated by $$V_{AC}(t) \approx I * [R_S + t/C_P], \ 0 \le t \le D \qquad \text{Eq. (1)}$$

To maintain proper operation of the TENS stimulator for delivering a current pulse of amplitude I and duration D, the high voltage $V_P$ must be set high enough to ensure $V_{CS}$ is at least $V_{CS}^{min}$. The required anode voltage $V_A$ reaches its maximum value $V_A^{max}$ at time D, and the maximum value is approximately $$V_A^{max} = V_{AC}(D) + I * R_I + V_{CS}^{min} = I * (R_S + R_I) + V_{CS}^{min} + \left(\frac{I}{C_P}\right) * D$$

where $R_I$ 355 is a sensing resistor with a known value internal to the TENS stimulator for measuring the actual current delivered to the stimulator load 350. In a preferred embodiment of the present invention, the voltage $V_I$ across the sensing resistor $R_I$ is measured via an analog-to-digital converter ADC 311 and the microprocessor µPC 312 then calculates the actual current delivered to the load 350 by dividing the voltage value $V_I$ by the resistance value of $R_I$. In a preferred embodiment of the present invention, the value of $R_I$ is set to 10$\Omega$. Therefore, the target output voltage $V_P$ must be set minimally at the value $V_A^{max}$ in order for the TENS stimulator to deliver current pulses with the required amplitude and duration. In a preferred embodiment, $V_{AC}(D)$ is not directly measured. Rather, the voltage $V_C$ is measured by the measurement circuit MMC 314 at time t=D or at a slightly earlier time. High voltage circuit output $V_P$ is adjusted through microprocessor μPC 312 so that voltage $V_C$ is as close as possible to zero at the end of the stimulation pulse duration D while maintaining the current amplitude during the pulse duration D.

The setting of the high voltage $V_P$ directly affects battery life. Nominal voltage of a battery $V_B$ 305 is about 4.2 volts. A high-voltage generating circuit 310 is used to step-up the battery nominal voltage to the required high voltage $V_P$. Power conservation principles dictate the following relationship between battery current draw $I_B$ 301 and high voltage $V_P$ at 309:

$$\beta * I_B * V_B = I * V_P * D/T$$

where β (<100%) is the high-voltage circuit efficiency. For a battery of a given capacity $Q_B$, the time $T_B$ for the battery capacity to deplete is given by $$T_B = \frac{\beta * Q_B * T * V_B}{I * D * V_P}$$

The actual battery life is shorter than, but proportional to, this theoretical upper bound. It will, therefore, be appreciated that battery life can be improved if the high voltage $V_P$ can be maintained at the minimum value that is required to deliver a desired stimulation pulse of amplitude I and duration D.

Maximizing Battery Life Through the Use of Novel Biphasic Waveform with Asymmetric Phase Morphology and Novel Arrangement of TENS Electrodes The novel TENS stimulator of the present invention is designed to maximize battery life (i.e., maximize $T_B$) while maintaining the TENS therapeutic effectiveness. More particularly, the novel TENS stimulator of the present invention utilizes biphasic stimulation pulses (instead of monophasic pulses). The addition of a second phase with reversed polarity minimizes skin irritation due to acid or alkaline reactions. In accordance with the present invention, a novel asymmetric biphasic stimulation pulse morphology is used which leverages the "voltage multiplier effect" (see below) to maximize the stimulation intensity effect of both phases of the pulse without increasing high voltage settings. Significantly, a novel electrode placement scheme allows both positive and negative phases of each biphasic stimulation pulse to effectively activate peripheral nerves for pain relief.

In this application, the word "asymmetric" is used to describe differences in the electrical current profiles of the two phases of a biphasic stimulation pulse. In addition, the word "asymmetric" is used to describe differences in the geometric areas of the two phases of a biphasic stimulation pulse. The area of an electrical stimulation pulse corresponds to the total charge delivered. Therefore, an asymmetric biphasic stimulation pulse may deliver unequal charges in each of the two phases of the biphasic stimulation pulse, causing the total charge delivered in the asymmetric biphasic stimulation pulse to be unbalanced (i.e., causing the accumulation of a "net" positive charge or a "net" negative charge under an electrode at the end of the second phase of the biphasic stimulation pulse).

Figure 4:
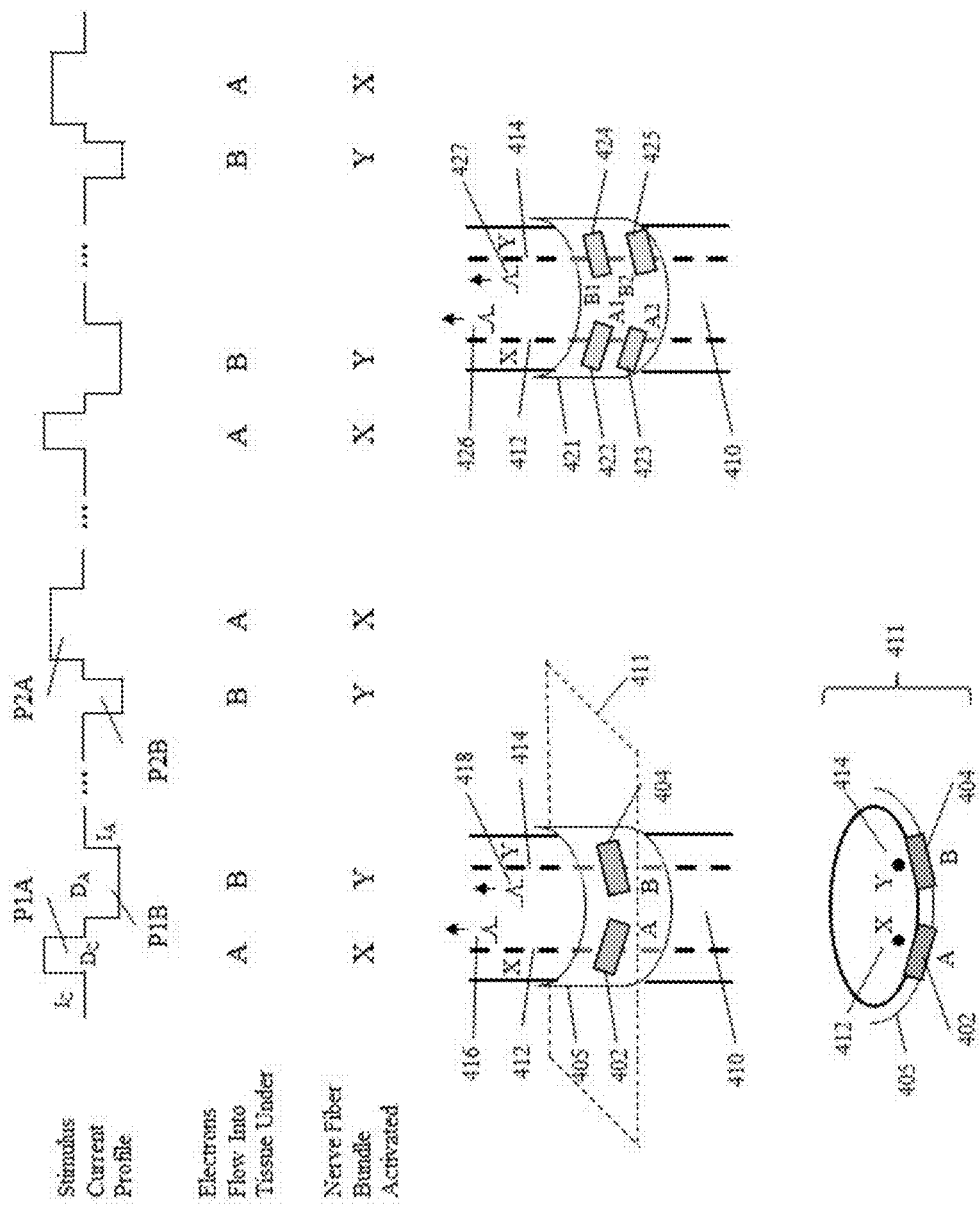
FIG. 4 is a schematic view of novel arrangements of TENS electrodes placed on the lower leg of a user for delivering asymmetric biphasic stimulation pulses regulated by the novel TENS stimulator shown in FIG. 3.

In a preferred embodiment of the present invention, two electrode pads are placed on the user's body in such a way that each electrode pad overlays a distinct set of nerve fibers. FIG. 4 provides an illustrative example. More particularly, an electrode array 405 with two electrodes (e.g., electrode A 402 and electrode B 404) is placed on the lower leg 410 of a user, with the two electrodes aligned approximately on the same cross-sectional plane 411. Preferably, electrode array 405 comprises a substrate having electrode A 402 and electrode B 404 mounted thereto with a predetermined configuration, wherein the substrate is configured to be held against the skin of the patient in a band-like matter. By way of example but not limitation, the TENS device may be configured as an adjustable band for mounting circumferentially around the limb of the user, with electrode array 405 being secured to the skin-facing side of the TENS device and captured against the skin of the patient. See, for example, U.S. Pat. No. 8,948,876, issued Feb. 3, 2015 to NeuroMetrix, Inc. and Shai N. Gozani et al. for APPARATUS AND METHOD FOR RELIEVING PAIN USING TRANSCUTANEOUS ELECTRICAL NERVE STIMULATION, which patent is hereby incorporated herein by reference. Because peripheral nerves in the lower leg region primarily traverse in the proximal-to-distal direction, each electrode 402, 404 will overlay a different nerve (e.g., electrode A 402 will overlay nerve X 412 and electrode B 404 will overlay nerve Y 414). In this context, the term "nerve" is used, without limitation, to refer to a collection of nerve fibers such as from a major peripheral nerve or a branch of a peripheral nerve. By forming electrode array 405 as a substrate with electrodes 402, 404 mounted thereto with a predetermined configuration, and by appropriately sizing electrode array 405 for the target anatomy, electrodes 402, 404 may be quickly and easily positioned to overlay the appropriate nerves (e.g., nerve X 412 and nerve Y 414) when electrode array 405 is secured to the remainder of the TENS device and the TENS device is mounted to the limb of the patient in a band-like manner. The two electrodes 402, 404 are electrically connected to the cathode and anode terminals 303, 302 of the TENS stimulator unit (FIG. 3).

During the stimulation pulse segment HA (i.e., the first phase of the first biphasic pulse), nerve X 412 under electrode A 402 is activated by electrical stimulation with intensity $IN_{1A}=I_C*D_C$ and the resulting nerve pulses 416 travel proximally to contribute to the effective dose for pain relief. During the stimulation pulse segment P1B (i.e., the second phase of the first biphasic pulse), nerve Y 414 under electrode B 404 is activated by electrical stimulation with intensity $IN_{1B}=I_A*D_A$ and the resulting nerve pulses 418 travel proximally to contribute to the effective dose for pain relief. Significantly, even though the temporal separation between stimulation pulse segment P1A and stimulation pulse segment P1B is typically 0.1 milliseconds or shorter (i.e., less than the refractory period of a peripheral nerve), nerves X and Y are activated only once (by either stimulation pulse segment P1A or stimulation pulse segment P1B) due to the non-overlapping nature of the nerves, and therefore nerve fibers, under the electrodes and the disposition of the electrodes relative to the nerves. Therefore, both nerves X 412 and Y 414 can be activated during the first biphasic pulse (i.e., nerve X can be activated during the first phase of the biphasic pulse and nerve Y can be activated during the second phase of the biphasic pulse) and contribute to the overall effective dose for pain relief. Because each phase of the biphasic pulse activates a separate nerve with resulting nerve pulses contributing to the effective dose for pain relief, the effective charge $C_E$ is the same as the total pulse charge of $(I_C^* D_C + I_A^* D_A)$ of this biphasic pulse. Stated another way, by applying the biphasic stimulation pulse across two electrodes, wherein each electrode overlies a different nerve, one electrode can activate one nerve during the first phase of the biphasic pulse and the other electrode can activate a second nerve during the second phase of the biphasic pulse. Therefore, each phase of the biphasic pulse operates to provide therapeutic nerve stimulation to the user, and the effective charge $C_E$ is provided by both phases of the biphasic pulse. As a result, with the electrode arrangement shown in FIG. 4, the effective charge $C_E$ delivered to the user with a biphasic pulse is $(I_C^* D_C) + (I_A^* D_A)$; by contrast, with the electrode arrangement shown in FIG. 2, the effective charge $C_E$ delivered to the user with a biphasic pulse is $(I_C^* D_C)$.

The next biphasic stimulation pulse (i.e., stimulation pulse segment P2B and stimulation pulse segment P2A) occurs at approximately 125 milliseconds (80 Hertz) after the first biphasic stimulation pulse, allowing both nerves time to recover from their respective refractory period and to be activated again. During the stimulation pulse segment P2B, the nerve Y 414 under electrode B 404 is activated by electrical stimulation with intensity $IN_{2B} = I_C^* D_C$. Similarly, the nerve X 412 under electrode A 402 is activated during the stimulation pulse segment P2A with intensity $IN_{2A} = I_A^* D_A$. Again the effective charge $C_E$ delivered by the biphasic stimulation pulse using the electrode configuration of FIG. 4 is the same as the total pulse charge of $(I_C^* D_C) + (I_A^* D_A)$ of this biphasic pulse. Therefore, the effective charge for each biphasic pulse increases to $(I_C^* D_C) + (I_A^* D_A)$ with the novel electrode arrangement of FIG. 4, which is significantly greater than the effective charge $I_C^* D_C$ using the electrode arrangement 245 of FIG. 2.

Other electrode placements have also been considered. More than one electrode can be connected to the anode and cathode connectors of the TENS stimulator unit. Electrodes may also be placed on the body in such a manner that the nerves underneath the electrodes connected to the cathode terminal are also partially under the electrodes connected to the anode terminal. Additionally, not all electrodes need to be connected to either cathode or anode terminals during stimulation. Electrode array 421 in FIG. 4 provides an example. Electrodes A1 422 and B1 424 are first connected to the cathode and anode terminals respectively to transmit one or more biphasic pulses. Then electrodes A2 423 and B2 425 are connected to the cathode and anode terminals for the next one or several biphasic pulses. Then electrode A1 422 and B2 425 are connected to the cathode and anode terminals again. Then electrodes A2 423 and B1 424 are connected to the cathode and anode terminals again. One advantage of alternating the electrode connections may be a reduction of nerve habituation as the relative timing of the nerve pulses 426 and 427 (traveling along the two nerve fiber bundles X 412 and Y 414) becomes variable.

In a preferred embodiment, the target nerve which is to be stimulated is a peripheral sensory nerve. In another preferred embodiment, the target nerve is a cutaneous branch of a mixed motor and sensory nerve.

Figure 5:
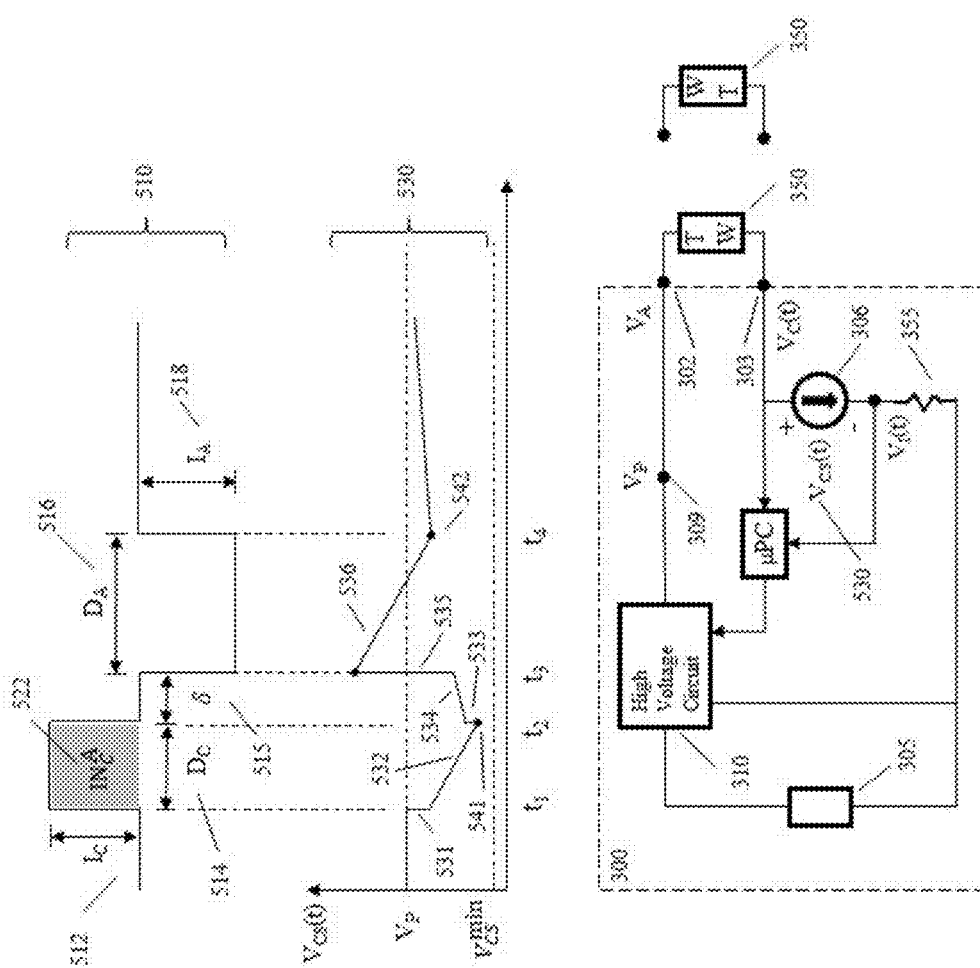
FIG. 5 is a schematic view of an asymmetric biphasic stimulation current pulse and associated voltage profile on the current source of the novel TENS stimulator shown in FIG. 3 when the biphasic stimulation current pulse is applied to a human body as modeled by a resistor-capacitor network.

FIG. 5 shows an illustrative example of the voltage profile $V_{CS}(t)$ 530 across the current source 306 corresponding to the biphasic stimulation pulse 510. Voltage $V_{CS}(t)$ starts out at $V_P$ when $t < t_1$ because voltages on all other components to the right of high voltage circuit 310 are zero as a result of zero current amplitude. At time $t = t_1$, there is an immediate voltage drop 531 across the resistive components $R_S$ 352 and $R_I$ 355 (FIG. 3) due to stimulation current. Between the time interval $t_1 \le t \le t_2$, the capacitive component $C_P$ 351 (FIG. 3) is being charged and the voltage across the load 350 causes a further gradual drop 532 of the voltage $V_{CS}(t)$. As long as minimum voltage 541 of $V_{CS}(t)$ stays above $V_{CS}^{min}$, or $V_{CS}(t_2) \ge V_{CS}^{min}$, the current source will function properly during the first phase 514 of the biphasic pulse and deliver stimulation at the required current amplitude $I_C$ 512. At time instance $t = t_2$, the current source 306 is turned off and any voltage across the resistive components $R_S$ and $R_I$ will become zero, causing a sudden increase 533 of $V_{CS}(t)$. During the time period $t_2 < t < t_3$, the current source 306 remains off and the capacitive component $C_P$ 351 (FIG. 3) in the load 350 discharges slightly through the resistive component $R_P$ 353 (FIG. 3), causing a slight increase 534 of $V_{CS}(t)$. In a preferred embodiment, the delay $\delta (=t_3-t_2)$ 515 is set to 100 microseconds. At time instance $t = t_3$, the load is reversed so that the original voltage drop in the direction from point T to point W in the load 350 becomes a voltage increase from point W to point T since voltage across the capacitor $C_P$ 351 (FIG. 3) cannot be changed instantaneously. As a result, the voltage $V_{CS}(t)$ across the current source 306 experiences a sudden increase 535 to a level usually above $V_P$. Between the time interval $t_3 < t < t_4$, the capacitive component $C_P$ is being charged and the voltage across the load 350 causes another gradual drop 536 of the voltage $V_{CS}(t)$. Again, as long as the minimum voltage 542 of $V_{CS}(t)$ stays above $V_{CS}^{min}$, or $V_{CS}(t_4) \ge V_{CS}^{min}$, the current source will function properly during the second phase 516 of the biphasic pulse and deliver stimulation at the required current amplitude $I_A$ 518.

Figure 6:
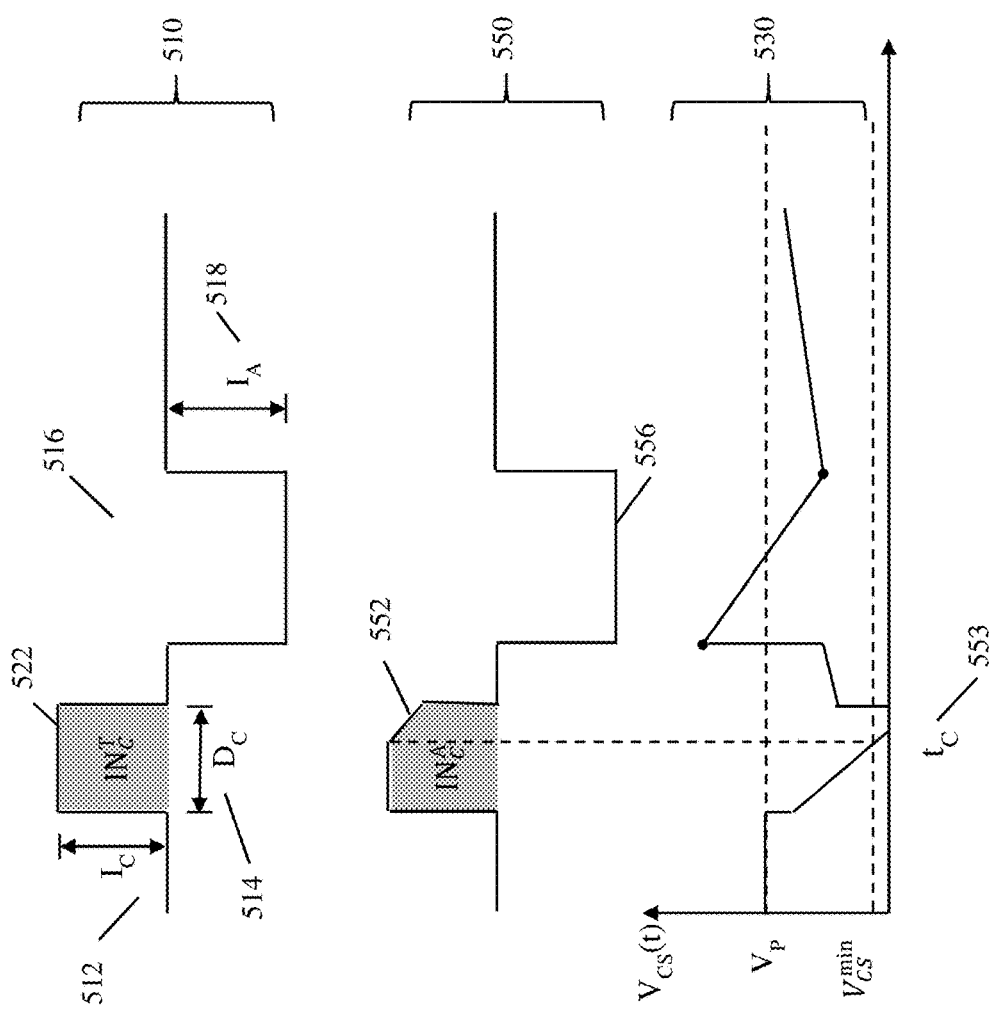
FIG. 6 is a schematic view of targeted and actual biphasic stimulation current pulse and associated voltage profile of the novel TENS stimulator shown in FIG. 3 when the voltage falls below the target value to cause actual stimulation current pulse profile to be different from the target profile.

If the voltage $V_P$ at output terminal 309 of the high voltage circuit 310 is set too low, the voltage $V_{CS}(t)$ 530 across the current source 306 may not stay above its minimum voltage requirement $V_{CS}^{min}$ during the first phase of the pulse, or the second phase of the pulse, or both phases of the pulse. When the voltage $V_{CS}(t)$ falls below $V_{CS}^{min}$, the current source may not be able to deliver the stimulation current at the required amplitude. FIG. 6 provides an illustrative example of the actual current pulse delivered 550 compared with the targeted stimulation current pulse 510. In this case, the first phase of the stimulation current pulse 552 fails to maintain the targeted stimulation current amplitude $I_C$ during the entire first phase of the biphasic stimulation pulse while the second phase of the stimulation current pulse 556 matches the targeted stimulation current amplitude $I_A$ throughout the entire second phase of the biphasic stimulation pulse. At time instance $t_C$ 553, the voltage $V_{CS}(t)$ falls below the threshold $V_{CS}^{min}$ because of the voltage increase across the capacitor $C_P$ (351 in FIG. 3) as a result of the capacitor being charged by the stimulation current $I_C$. Actual stimulation current amplitude can be monitored via voltage readings from the resistor $R_1$ as described above. If the actual stimulation current amplitude is not maintained at the same level throughout the entire phase duration, its stimulation intensity is no longer $I_C^* D_C$. The actual stimulation intensity is the size of the shaded area 552 and can be approximated by a summation of a series of stimulation current amplitude measurements multiplied by the time interval between the consecutive current measurements. The shaded area 522 sometimes is referred to as the actual charge delivered by the stimulator during the first phase. In one embodiment, if the actual charge delivered is 10% (error percentage) smaller than the target charge $I_C^* D_C$, the voltage $V_P$ is adjusted higher by an amount proportional to the error percentage value.

The voltage $V_P$ at output terminal 309 of the high voltage circuit 310 is regulated so that it stays as low as possible while maintaining the integrity of the stimulation pulse. In one embodiment, the integrity of the stimulation pulse is defined as the amplitude of the stimulation current I(t) of the biphasic stimulation pulse 510 being within a predetermined percentage of the target value $I_C$ for all $t_1 \leq t \leq t_2$ and the target value $I_A$ for all $t_3 \leq t \leq t_4$. An example of this predetermined percentage value is 95%. In another embodiment, the integrity of the stimulation pulse is defined as the intensity $IN_C^A$ 552 being within a predetermined percentage of the target intensity value $IN_C^T = I_C * D_C$. An example of this predetermined percentage value is 90%. The actual amplitude of the stimulation current delivered can be measured via the voltage drop $V_I(t)$ across the resistor $R_I$ 355 over time.

Figure 7:
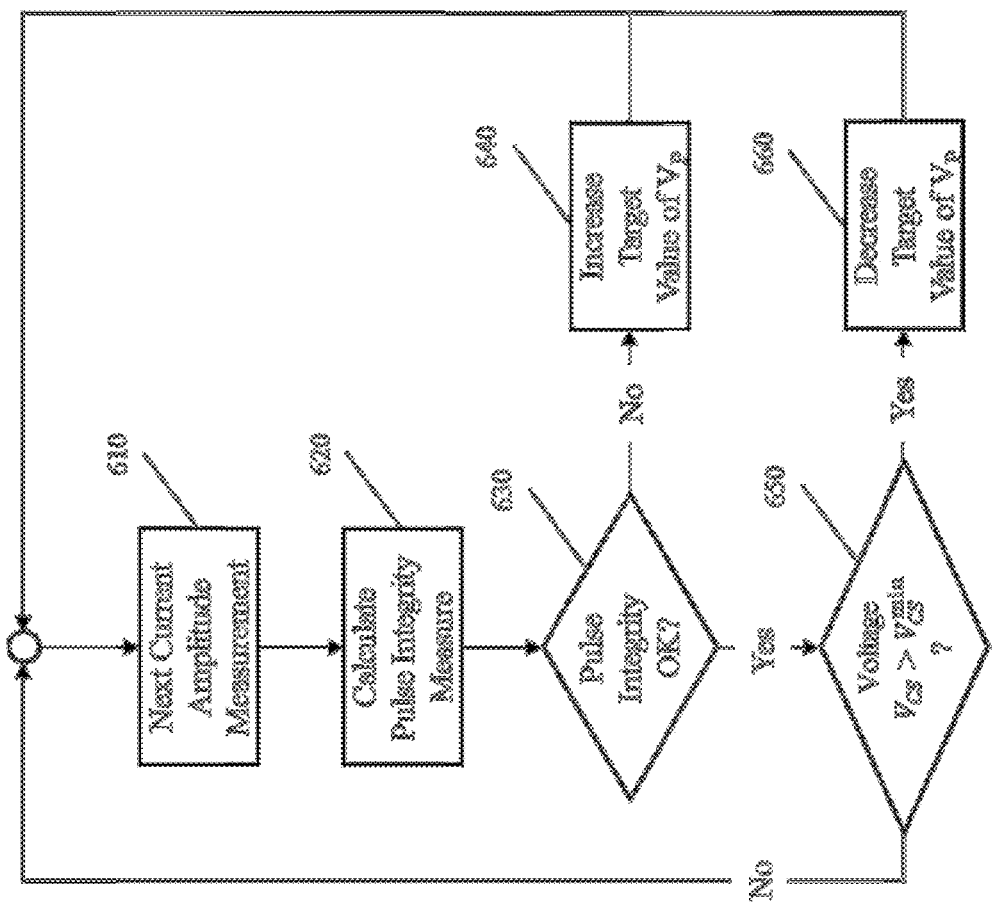
FIG. 7 is a schematic flowchart showing exemplary operation of the novel TENS stimulator shown in FIG. 3 to regulate the high voltage circuit output for increasing battery efficiency.

FIG. 7 shows a flowchart of a high voltage control algorithm to regulate the high voltage $V_P$. The actual amplitude of the stimulation current delivered I(t) can be measured via voltage $V_I$ across the resistor $R_I$ 355. Step 610 determines the actual stimulation current amplitude. Depending upon the exact definition of the pulse integrity, the most recent current amplitude or the integration of current amplitude measurements are obtained in step 620. The pulse integrity value is compared against appropriate threshold values to determine whether the pulse integrity is acceptable in step 630. If the integrity is not OK, the target value of the high voltage circuit output $V_P$ is increased through step 640 and the stimulation current amplitude is measured again at a pre-determined time interval. If the integrity is found to be OK in step 630, then the voltage $V_{CS}(t) = V_C(t) - V_I(t)$ is obtained in step 650. If the voltage exceeded the minimum threshold $V_{CS}^{min}$, then the target value of the high voltage circuit output $V_P$ is decreased through step 660. In a preferred embodiment, $V_{CS}^{min} = 1$ Volt.

As seen in FIG. 5, the voltage $V_{CS}(t)$ decreases during the first phase 514 of the biphasic stimulation pulse and during the second stimulation phase 516 of the biphasic stimulation pulse. The sizes of the decreases 532 and 536 are proportional to the stimulation intensity $I_C*D_C$ and $I_A*D_A$, respectively. For the first phase 514 of the biphasic pulse, the stimulation intensity is limited by $V_P - I_C(R_S + R_I) - V_{CS}^{min}$, or the maximum voltage drop possible on the capacitor $C_P$ 351 within the load 350. However, the stimulation intensity upper limit for the second phase 516 of the biphasic pulse is twice as large as that for the first phase 514 of the biphasic pulse: $2*(V_P - I_C(R_S + R_I) - V_{CS}^{min})$. This is because the voltage on the capacitor $C_P$ is added to $V_P$ at time instance $t = t_3$ so as to provide the starting voltage at the cathode terminal 303. Thus, the upper limit of the stimulation intensity for the second phase 516 of the biphasic pulse is twice as large as the upper limit of the stimulation intensity for the first phase 514 of the biphasic pulse. This phenomenon is sometimes referred to as the "voltage multiplier effect". In practice, the value of the voltage multiplier effect is smaller than 2 due to discharge of the capacitor $C_P$ during the time period $t_2 \leq t \leq t_3$ and leakage currents in the stimulator circuit.

The amplitude and duration parameters of each phase 514, 516 of the biphasic pulse can be independently specified. In one embodiment, $I_C$ (the stimulation current amplitude of the first phase) and $I_A$ (the stimulation current amplitude of the second phase) are set to one common value, and $D_C$ (the duration of the first phase) and $D_A$ (the duration of the second phase) are set to another common value. This configuration is the traditional biphasic symmetrical waveform. In another embodiment, $I_C$ and $I_A$ are set to the same value, but $D_A$ is set to be longer than $D_C$ in order to take advantage of the aforementioned voltage multiplier effect of the stimulator circuit (which is due to the electric charge accumulated in the capacitor $C_P$ during the first phase of the biphasic pulse). This configuration is a biphasic asymmetrical waveform.

In yet another embodiment, the amplitude of the second phase $I_A$ is set to a value higher than $I_C$ so that $Q_C = I_C*D_C$ is the same as $Q_A = I_A*D_A$ (thus $D_A < D_C$). Setting $I_A$ higher than $I_C$ may not require a higher target value for high voltage circuit output $V_P$ because of the aforementioned voltage multiplier effect. Being able to set $I_A$ higher, without requiring a higher output voltage $V_P$, has several advantages. One of these advantages is to allow more effective stimulation of the nerve due to the well-known strength-duration relationship governing nerve stimulation efficacy. The charge required to stimulate a nerve fiber, $Q^{TH}$, increases linearly with the stimulation duration D as follows $$Q^{TH} = b*(D+c)$$

where b and c are constants called the rheobase and chronaxie, respectively. These constants are influenced by many factors that include the biophysical properties of the nerve fiber being stimulated, the characteristics of the intervening tissue between the electrode and nerve fiber, and the characteristics of the stimulation waveform. However, in all cases b>1 and c>0. Therefore, the same nerve fiber will have a lower $Q^{TH}$ if it is subject to a stimulation pulse with a higher amplitude I and shorter duration D. In other words, stimulation pulses with the same intensity, but a shorter duration, are more effective than those with a longer duration.

In yet another embodiment, both amplitude $I_A$ and duration $D_A$ of the second phase of the biphasic pulse can be set higher than their corresponding values of the first phase without the need to increase the high voltage circuit output $V_P$ due to the aforementioned voltage multiplier effect.

In yet another embodiment, the amplitude of the second phase $I_A$ is set to a different value, for example in a random fashion, for consecutive biphasic pulses such that all amplitude values are within a range. The lower limit of the range can be the amplitude of the first phase $I_C$ and the upper limit of the range can be the highest value without increasing the high voltage circuit output $V_P$ requirement that is needed to support the first phase of the biphasic pulse stimulation. The duration of the second phase of the biphasic stimulation pulse can similarly be set to a range of values. An advantage of varying the intensity of the second phase of the biphasic pulse is to reduce nerve habituation and to increase TENS analgesia effectiveness.

With the same high voltage circuit output $V_P$, the second phase of the biphasic stimulation pulse is capable of stimulating a nerve whose $Q^{TH}$ may exceed what the first phase of the biphasic stimulation pulse may be able to do, even when $V_P = V_P^{max}$, where $V_P^{max}$ is the maximum output voltage that can be delivered by the high voltage circuit 310. In another embodiment, the high voltage circuit output $V_P$ is adjusted to a level only high enough to guarantee the integrity of the second phase of the biphasic stimulation pulse. At least two advantages are obtained with such an approach. Firstly, by leveraging the voltage multiplier effect at the second phase of the biphasic pulse, some pain relief can be provided to users of the TENS device whose $Q^{TH}$ cannot be supported with the existing TENS hardware design specifications if only monophasic pulses are used. Secondly, battery life can be extended inasmuch as the high voltage circuit output is lower than what would otherwise be required.

If the amplitude of the stimulation current remains the same for both phases of the biphasic stimulation pulse (i.e., $I_C = I_A = I$), one can optimize the duration ratio between the two phases of the biphasic pulse to maximize the total intensity of the biphasic pulse for a given high voltage $V_P$. For simplicity, we assume $D_C=\alpha*D_S$ and $D_A=(1-\alpha)*D_S$, where $D_S$ is the summation of the first and second phases of the biphasic pulse. Thus α represents the ratio of the duration of the first phase of the biphasic pulse to the sum of the durations of the first phase of the biphasic pulse plus the second phase of the biphasic pulse. Consequently, the total intensity delivered would be $I*D_S$. Recall earlier that we have shown that the voltage over the current source 306 is $V_P-I(R_S+R_I)-V_E^C$, where $V_E^C$ is the voltage across the capacitor $C_P$ as a result of a current pulse with amplitude I and duration $\alpha D_S$: $V_E^C=\alpha*I*D_S$. The minimum required high voltage output is $V_P^{min}=V_E^C+I(R_S+R_I)+V_{CS}^{min}$. Ignoring the voltage change 534 due to capacitor $C_P$ discharge during the inter-phase interval 6 515 (FIG. 5), the voltage over the current source 306 at the beginning of second phase is (at t=

$$V_P^{min}+V_E^C-I*(R_S+R_I)=2V_E^C+V_{CS}^{min}$$

The maximum voltage change $\Delta V_E^{A,max}$ over the capacitor 351 during the second phase of the biphasic pulse must satisfy $$2V_E^C+V_{CS}^{min}-\Delta V_E^{A,max}\geq V_{CS}^{min} \text{ or } \Delta V_E^{A,max}\leq 2V_E^C$$

Utilizing the aforementioned Eq. (1), we have $$(1-\alpha)*I*D_S\leq 2*I*D_S \text{ or } \alpha\geq \frac{1}{3}.$$

In a preferred embodiment, the value α is set to 0.36. Using the approximation of $I(R_S+R_I)+V_{CS}^{min}\approx \gamma V_E^C$, where $\gamma \ll 1.0$ is a constant, we have the minimum required high voltage for a given α as $$V_P^{min}=(1+\gamma)*V_E^C=(1+\gamma)*\alpha*I*D_S$$

For a fixed effective charge (total stimulation intensity) $I*D_S$, the minimum high voltage setting at α=0.36 is $$\frac{0.36}{0.5}=72\%$$

of what would be required for a symmetric biphasic pulse (i.e., a biphasic pulse having equal duration for both phases, or α=0.5). As a result, battery life is expected to be 39% longer under the asymmetric pulse duration case (α=0.36) than under the symmetric pulse duration case (α=0.5) when both cases deliver the same effective charge $I*D_S$.

Achieving Net Zero Charge Accumulation by Reversing the Polarity of the Biphasic Pulses In one form of the present invention, each biphasic pulse has unbalanced total charge for its two phases. See, for example, the biphasic waveform shown in FIG. 5. The total charge of the first phase of the biphasic pulse is not balanced by the total charge of the second phase of the biphasic pulse: $I_C*D_C\neq I_A*D_A$. Accordingly, in one preferred embodiment of the present invention, the polarity of the leading phase of consecutive biphasic pulses alternates so as to allow balanced charge to be delivered to each electrode skin contact area. More particularly, and looking at FIG. 4, the total (negative) charge flowing into the skin area under electrode A 402 is $I_C*D_C$ during the first phase H A of the biphasic pulse and the total (negative) charge flowing out of the skin area is $I_A*D_A$ during the second phase P1B of the biphasic pulse. The second biphasic pulse has the polarity of its leading phase P2B reversed when compared with the polarity of the leading phase P1A of the first biphasic pulse. Consequently, the total (negative) charge flowing out of the skin area is $I_C*D_C$ during the first phase P2B of the biphasic pulse and the total (negative) charge flowing into the skin area is $I_A*D_A$ during the second phase P2A of the biphasic pulse. So the net charge is effectively balanced over a span of two biphasic pulses. Similarly, there is no net charge accumulation in the skin areas under electrode B 404.

Instead of alternating the polarity of the leading phase for every biphasic pulse (i.e., as shown in FIG. 4), the frequency of alternating the polarity of the leading phase of the biphasic pulses can be set to a lower value as long as the zero net charge accumulation is maintained across a reasonable period of time. In other words, the polarity of the leading phase of the biphasic pulses may be changed every two pulses, or every three pulses, or every four pulses, etc., so long as there is no net charge accumulation over a selected period of time (which is not so long as to result in adverse skin reactions under the electrodes). In one preferred embodiment, polarity alternating occurs every two biphasic pulses.

Experimental Data Demonstrating Benefits of Asymmetric Biphasic Pulse Stimulation To demonstrate the benefits of the asymmetric pulse duration approach disclosed herein, ten healthy subjects were recruited and consented to participate in a study to compare the effectiveness of two different biphasic pulse stimulation patterns. Pattern A was the symmetric biphasic pulse pattern wherein both phases of the biphasic pulse had the same amplitude and duration, e.g., such as the biphasic pulse pattern shown in FIG. 2. The duration was fixed at 100 microseconds and amplitude was allowed to be adjusted by each subject to evoke the first sensation of electrical stimulation. Pattern B was the asymmetric biphasic pulse pattern wherein the second phase of the biphasic pulse had a longer duration (180 microseconds) than the first phase of the biphasic pulse (100 microseconds), e.g., such as the biphasic pulse pattern shown in FIG. 5. The amplitude of both phases of the Pattern B asymmetric biphasic pulse pattern was kept the same and allowed to be adjusted by each subject so as to evoke the same first sensation of electrical stimulation as for Pattern A. Subjects were blinded to the stimulation pattern used and carried out the sensation threshold discovery process three times for each stimulation pattern. During each trial, the subject indicated the minimum stimulation pulse amplitude that evoked the first sensation of electrical stimulation. Table 1 summarizes the study results. For each subject, the three identified stimulation pulse amplitudes (in milliamps) were averaged for Pattern A and Pattern B, respectively. Among the ten test subjects, the minimum stimulation current amplitude to evoke a first sensation of electrical stimulation was 14%-35% lower for asymmetric pulse pattern B than that for symmetric pulse pattern A. Since both pulse patterns had the same duration in the first phase of the biphasic pulse, the reduction in stimulation current amplitude required to evoke the first sensation can only be attributed to longer duration of the second phase of the asymmetric pulse Pattern B. Earlier analyses indicate that the minimum high voltage $V_P$ required will be lower if the first phase current amplitude is lower. Because of the voltage multiplier effect, the high voltage requirement for any pulse with a second phase duration less than 2-times the first phase duration will be approximately the same as that for the first phase.

TABLE 1

| SubjID | Pattern B | Pattern A | Difference (mA) | Difference (%) |
|--------|-----------|-----------|-----------------|----------------|
| 1      | 10.0      | 14.8      | −4.8            | −32.2%         |
| 2      | 12.1      | 16.9      | −4.7            | −28.2%         |
| 3      | 13.9      | 21.3      | −7.3            | −34.5%         |
| 4      | 9.1       | 13.6      | −4.5            | −32.9%         |
| 5      | 17.5      | 22.3      | −4.8            | −21.6%         |
| 6      | 12.5      | 14.5      | −2.1            | −14.4%         |
| 7      | 9.8       | 14.3      | −4.4            | −31.0%         |
| 8      | 11.8      | 15.9      | −4.1            | −25.8%         |
| 9      | 14.0      | 16.6      | −2.6            | −15.7%         |
| 10     | 7.1       | 10.3      | −3.2            | −30.7%         |
| Mean   |           |           |                 | −26.7%         |

Comparison of minimum current amplitude required to evoke first stimulation sensation in human subjects. Pattern A refers to biphasic pulse with same pulse duration for both phases (100 μs). Pattern B refers to biphasic pulse with the pulse duration for second phase (180 μs) longer than the first pulse duration (100 μs). Amplitude for both phases are the same in either pulse patterns. Results are the average of three trials.

Direct Muscle Stimulation Using Asymmetric Biphasic Electrical Pulses with an Alternating Polarity of the Leading Phase of the Pulses Electrical pulses can also be used to stimulate muscles directly so as to cause muscle contractions. Electrical pulses are delivered through electrodes on the skin. Instead of placing the electrodes so as to overlay peripheral nerves, the electrodes are placed on the skin in direct proximity to the muscles which are to be stimulated. Electrical muscle stimulation (EMS) can be used to improve muscle strength in athletes, to prevent muscle atrophy in patients with musculoskeletal injuries, and to provide external muscle control when the nerve supply to the muscle is compromised.

Portable EMS devices face similar challenges to TENS devices in terms of battery life and stimulation intensity. Applying asymmetric biphasic stimulation pulses in EMS can overcome these challenges by leveraging charge build-up during the first phase of the biphasic stimulation pulse in order to deliver more powerful stimulation during the second phase of the biphasic stimulation pulse. Delivering stronger stimulation pulses with a higher amplitude or a longer duration in the second phase of the biphasic stimulation pulse, without requiring an increase in the output of the high-voltage circuit, will lead to savings in battery life. Alternating the polarity of the leading phase of the biphasic electrical pulses allows the muscles under each electrode to receive the same total stimulation intensity. Alternating the polarity of the leading phases of the biphasic electrical pulses also ensures zero net charge flowing into each electrode even when asymmetric biphasic pulses are used.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for providing transcutaneous electrical muscle stimulation to a user, said apparatus comprising:
a stimulation unit for electrically stimulating one or more muscles using an asymmetric biphasic electrical pulse from a current source, wherein during the first phase and the second phase of an asymmetric biphasic electrical pulse, said stimulation unit uses a same voltage level at an anode, wherein said stimulation unit delivers a larger amount of electrical charge in the second phase of the asymmetric biphasic electrical pulse than the amount of electrical charge delivered in the first phase of the asymmetric biphasic electrical pulse, and wherein the same anode voltage level is selected to maintain a minimum voltage required for the current source during the first phase of the asymmetric biphasic electrical pulse;
a control unit for controlling the stimulation delivered by said stimulation unit; and
an electrode array connectable to said stimulation unit, said electrode array comprising a substrate and at least first and second electrodes.

2. Apparatus according to claim 1 wherein the at least first and second electrodes are mounted to said substrate with a predetermined arrangement, so that when said substrate is placed on one location of the user's body, said first electrode overlays a first muscle underneath the electrode array but not a second muscle underneath the electrode array and said second electrode overlays the second muscle underneath the electrode array but not the first muscle underneath the electrode array.

3. Apparatus according to claim 2 wherein the said first electrode and said second electrode both overlay a third muscle underneath the electrode array.

4. Apparatus according to claim 1 wherein said control unit is configured to cause said stimulation unit to deliver discrete asymmetric biphasic electrical pulses.

5. Apparatus according to claim 4 wherein the polarity of the first phase of the discrete asymmetric biphasic electrical pulses varies.

6. Apparatus according to claim 4 wherein the polarity of the first phase of each discrete asymmetric biphasic electrical pulse varies so as to ensure that an equal amount of positive and negative charges flow into each electrode within a predetermined time period.

7. Apparatus according to claim 4 wherein the discrete asymmetric biphasic electrical pulses are delivered at a constant frequency.

8. Apparatus according to claim 4 wherein the discrete asymmetric biphasic electrical pulses are delivered at a random frequency.

9. Apparatus according to claim 1 wherein said control unit controls the anode voltage of said stimulation unit.

10. Apparatus according to claim 9 wherein said control unit controls said anode voltage based on at least one of the following: (i) the cathode voltage, and (ii) measurements of the asymmetric biphasic electrical pulses.

11. Apparatus according to claim 1 wherein said control unit controls the amplitude and duration of the first and second phases of the asymmetric biphasic electrical pulses.

12. Apparatus according to claim 11 wherein the amplitude of the second phase of said asymmetric biphasic electrical pulses is the same as that of the first phase of said asymmetric biphasic electrical pulses.

13. Apparatus according to claim 11 wherein the amplitude of the second phase of said asymmetric biphasic electrical pulses is greater than that of the first phase of said asymmetric biphasic electrical pulses.

14. Apparatus according to claim 11 wherein the duration of the second phase of said asymmetric biphasic electrical pulses is the same as that of the first phase of said asymmetric biphasic electrical pulses.

15. Apparatus according to claim 11 wherein the duration of the second phase of said asymmetric biphasic electrical pulses is greater than that of the first phase of said asymmetric biphasic electrical pulses.

16. Apparatus for providing transcutaneous electrical muscle stimulation to a user, said apparatus comprising:
- a stimulation unit for electrically stimulating one or more muscles using an asymmetric biphasic electrical pulse from a current source, wherein during the second phase of the asymmetric biphasic electrical pulse, said stimulation unit uses an anode voltage level that is no greater than the anode voltage level used during the first phase of the asymmetric biphasic electrical pulse, and wherein said stimulation unit delivers a larger amount of electrical charge in the second phase of the asymmetric biphasic electrical pulse than the amount of electrical charge delivered in the first phase of the asymmetric biphasic electrical pulse;
- a control unit for controlling the stimulation delivered by said stimulation unit; and
- an electrode array connectable to said stimulation unit, said electrode array comprising a substrate and at least first and second electrodes.

17. A method for providing transcutaneous electrical muscle stimulation therapy to a user, said method comprising:
- providing a stimulation unit for generating asymmetric biphasic electrical pulses, wherein the stimulation unit delivers a larger amount of electrical charge in the second phase of an asymmetric biphasic electrical pulse than the amount of electrical charge delivered in the first phase of the asymmetric biphasic electrical pulse, and wherein a same anode voltage level is used by the stimulation unit during the first and second phases of the asymmetric biphasic electrical pulse;
- providing an electrode array connectable to said stimulation unit, said electrode array comprising a substrate and at least first and second electrodes; and
- using said stimulation unit and said electrode array to apply asymmetric biphasic electrical pulses to the skin of a user.

18. A method according to claim 17 wherein the at least first and second electrodes are mounted to said substrate with a predetermined arrangement, so that when said substrate is placed on one location of the user's body, said first electrode overlays a first muscle underneath the electrode array but not a second muscle underneath the electrode array and said second electrode overlays the second muscle underneath the electrode array but not the first muscle underneath the electrode array.

19. A method according to claim 18 wherein the first electrode activates the first muscle during the first phase of the asymmetric biphasic electrical pulse and the second electrode activates the second muscle during the second phase of the asymmetric biphasic electrical pulse.

20. A method according to claim 17 wherein said stimulation unit delivers a sequence of discrete asymmetric biphasic electrical pulses.

21. A method according to claim 20 wherein said asymmetric biphasic electrical pulses are delivered at a random frequency, wherein said random frequency is within a predetermined range.

22. A method according to claim 20 wherein said asymmetric biphasic electrical pulses vary the polarity of the first phase of the asymmetric biphasic electrical pulses.

23. A method according to claim 22 wherein the pattern of variations of the first phases of the asymmetric biphasic electrical pulses ensures that an equal amount of positive and negative charges flow into each electrode within a predetermined time period.

24. A method according to claim 17 wherein said stimulation unit controls the amplitude of the two phases of the asymmetric biphasic electrical pulses independently.

25. A method according to claim 17 wherein said stimulation unit controls the duration of the two phases of the asymmetric biphasic electrical pulses independently.

26. A method according to claim 17 wherein said stimulation unit controls the anode voltage based on at least one of the following: (i) the cathode voltage, and (ii) measurements of the asymmetric biphasic electrical pulses.

27. A method for providing transcutaneous electrical muscle stimulation therapy to a user, said method comprising:
- providing a stimulation unit for generating asymmetric biphasic electrical pulses, wherein the stimulation unit delivers a larger amount of electrical charge in the second phase of an asymmetric biphasic electrical pulse than the amount of electrical charge delivered in the first phase of the asymmetric biphasic electrical pulse, and wherein the stimulation unit uses an anode voltage level in the second phase that is no greater than the anode voltage level used in the first phase;
- providing an electrode array connectable to said stimulation unit, said electrode array comprising a substrate and at least first and second electrodes; and
- using said stimulation unit and said electrode array to apply asymmetric biphasic electrical pulses to the skin of a user.

* * * * *